US012651672B2

(12) United States Patent
Yerebakan et al.

(10) Patent No.: US 12,651,672 B2
(45) Date of Patent: Jun. 9, 2026

(54) CLINICAL DECISION SUPPORT

(71) Applicant: Siemens Healthcare GmbH, Erlangen (DE)

(72) Inventors: Halid Yerebakan, Malvern, PA (US); Yoshihisa Shinagawa, Downingtown, PA (US); Anna Jerebko, Paoli, PA (US); Ke Zeng, Bryn Mawr, PA (US); Simon Allen-Raffl, West Chester, PA (US); Gerardo Hermosillo Valadez, West Chester, PA (US)

(73) Assignee: SIEMENS HEALTHINEERS AG, Forchheim (DE)

(*) Notice: Subject to any disclaimer, the term of this patent is extended or adjusted under 35 U.S.C. 154(b) by 579 days.

(21) Appl. No.: 17/388,128

(22) Filed: Jul. 29, 2021

(65) Prior Publication Data

US 2022/0051805 A1 Feb. 17, 2022

(30) Foreign Application Priority Data

Aug. 13, 2020 (EP) .................................... 20190929

(51) Int. Cl.
*G16H 50/70* (2018.01)
*G06F 17/18* (2006.01)
*G16H 50/30* (2018.01)
(52) U.S. Cl.
CPC ............. *G16H 50/70* (2018.01); *G06F 17/18* (2013.01); *G16H 50/30* (2018.01)
(58) Field of Classification Search
CPC ........ G16H 50/70; G16H 50/30; G16H 10/60; G16H 10/20; G16H 50/20; G06F 17/18
See application file for complete search history.

(56) References Cited

U.S. PATENT DOCUMENTS 4,852,173 A * 7/1989 Bahl ....................... G10L 15/00
704/255
9,662,064 B2 * 5/2017 Vilsmeier ............ A61B 5/4842
10,446,273 B1 10/2019 McNair et al.
(Continued)

FOREIGN PATENT DOCUMENTS

EP 3910645 A1 11/2021
EP 4016543 A1 6/2022

OTHER PUBLICATIONS

Extended European Search Report dated Jan. 27, 2021.

*Primary Examiner* — Kambiz Abdi
*Assistant Examiner* — Tran N Nguyen
(74) *Attorney, Agent, or Firm* — Harness, Dickey & Pierce, P.L.C.

(57) ABSTRACT

A computer-implemented method is for clinical decision support. In an embodiment, the method includes receiving patient data of a target patient; determining, based on the patient data, a number of potential clinical outcomes associated with the target patient; calculating, for each respective potential clinical outcome, a respective probability of being indicated by the patient data; selecting, based on the plurality of probabilities calculated, one or more anamnestic questions from a set of anamnestic questions stored; presenting the one or more anamnestic questions selected to a user via a user interface; receiving one or more answers to the one or more anamnestic questions selected, from the user; and adapting the plurality of probabilities based upon the one or more answers received.

23 Claims, 9 Drawing Sheets

(56) References Cited

U.S. PATENT DOCUMENTS

| | | | |
|---|---|---|---|
| 10,687,751 B2 * | 6/2020 | Wall | A61B 5/7267 |
| 11,348,022 B2 * | 5/2022 | Douglas | G06F 17/16 |
| 2002/0029157 A1 * | 3/2002 | Marchosky | G16H 40/67 |
| | | | 705/3 |
| 2010/0082369 A1 * | 4/2010 | Prenelus | G16H 40/67 |
| | | | 705/3 |
| 2011/0166879 A1 * | 7/2011 | Lee | G16Z 99/00 |
| | | | 705/2 |
| 2012/0101846 A1 * | 4/2012 | Gotthardt | G16H 40/63 |
| | | | 705/3 |
| 2012/0301864 A1 | 11/2012 | Bagchi | |
| 2013/0035956 A1 * | 2/2013 | Carmeli | G06Q 10/10 |
| | | | 705/3 |
| 2013/0298192 A1 * | 11/2013 | Kumar | H04L 63/1425 |
| | | | 726/25 |
| 2014/0046683 A1 * | 2/2014 | Michelson | G16H 40/20 |
| | | | 705/2 |
| 2017/0042461 A1 * | 2/2017 | Hodas | G09B 7/00 |
| 2018/0211007 A1 * | 7/2018 | Cox | G06Q 30/0283 |
| 2018/0322635 A1 * | 11/2018 | Guo | G06T 7/12 |
| 2019/0043619 A1 * | 2/2019 | Vaughan | G16H 50/20 |
| 2019/0392952 A1 * | 12/2019 | Harris | G16H 40/60 |
| 2021/0358600 A1 | 11/2021 | Yerebakan et al. | |

* cited by examiner

CLINICAL DECISION SUPPORT

PRIORITY STATEMENT

The present application hereby claims priority under 35 U.S.C. § 119 to European patent application number EP 20190929.8 filed Aug. 13, 2020, the entire contents of which are hereby incorporated herein by reference.

FIELD

Example embodiments of the invention generally relate to clinical decision support systems and associated methods.

BACKGROUND

The patient journey involves a plethora of clinical decisions many of which directly impact on the wellbeing of the patient. Clinical decisions range from making the right diagnosis and finding the best therapy to providing a prognosis for the patient on that basis. In addition, a medical professional is supposed to decide on further actions such as follow-ups, referrals, or the enrollment of the patient for a clinical trial.

All of these decisions specifically depend on the details of the patient case. As healthcare delivery systems continue to accelerate and evolve, medical professionals today have the luxury of access to an abundance of medical data. However, this abundance of medical data is also a burden on medical personnel, who can be overwhelmed with data overload. To alleviate this, clinical decision support systems have been developed which are designed to provide physicians and other health professionals with assistance for clinical decision-making tasks. Typically, such systems rely on structured storage and access of data to bring relevant information to the attention of the user, to make suggestions, and to influence health choices of the user for improved health care.

One issue with existing systems is that they can only work with data they have access to. If one crucial piece of information is missing, the picture provided to the user may be incomplete. This may result in inappropriate suggestions which may cause unwanted psychological and sub-optimal downstream diagnostic and treatment consequences.

What is more, for many clinical decisions, the number of possible outcomes coming into question may be very high. Taking the task of deriving a medical diagnosis from image data as an example, there may be a considerable number of possible diseases which may be traced back to the patterns shown in an image. As a consequence, clinical decision support systems may retrieve a comparable huge number of possibilities each of which has a low confidence if taken alone.

SUMMARY

The inventors have discovered that the above becomes even more problematic, if the clinical decision system is to rank such outcomes. Here, tiny differences in the probabilities may tip the balance in favor of an outcome which, as such, does not have a high likelihood of being indicated or at least is not considerably more probable than other differential outcomes. Under such circumstances, automatically generated outcomes would still require considerable effort from the clinician as she or he needs to follow up on similar cases, ask colleagues for their input, and so forth. By consequence, the assistance provided by suchlike clinical decision support systems may be perceived as unreliable and exhaustive by the user.

At least one embodiment of the present invention addresses at least one of these issues and/or provides a method and/or system capable of providing improved clinical decision support. In particular, at least one embodiment of the present invention provides a method and/or system which can provide suggestions for clinical decisions in the form of potential clinical outcomes with higher confidence and less uncertainty.

Embodiments are directed to methods for clinical decision support, corresponding systems, a corresponding computer-program product and/or computer-readable storage medium. Alternative and/or preferred embodiments are subject of the claims.

In the following, embodiments of the present invention are described with respect to the apparatuses as well as with respect to the methods. Features, advantages or alternative embodiments described herein can likewise be assigned to other objects and vice versa. In other words, claims addressing the inventive method can be improved by features described or claimed with respect to the apparatuses. In this case, e.g., functional features of the method are embodied by objective units, modules, or elements of the apparatus.

According to an embodiment, a computer-implemented method for clinical decision support is provided. The method comprises a plurality of steps. A first step is directed to receiving patient data of a target patient. A further step is directed to determining a number of potential clinical outcomes associated with the target patient based on the patient data. A further step is directed to calculating, for each of the potential clinical outcomes, a probability of being indicated by the patient data. A further step is directed to selecting, as a function of the probabilities, one or more anamnestic questions from a set of pre-configured anamnestic questions stored in a database. A further step is directed to presenting the one or more selected anamnestic questions to a user via a user interface. A further step is directed to receiving one or more answers (or responses) to the one or more selected anamnestic questions from the user via the user interface. And yet a further step is directed to adapting the probabilities based upon the answers.

According to an embodiment, a system for clinical decision support is provided. The system comprises an interface unit, and a computing unit. The interface unit is configured to interface with a user of the system, a database storing a set of anamnestic questions and to receive patient data of a target patient. The computing unit is configured to determine, based on the patient data, a number of potential clinical outcomes for the target patient, to calculate, for each of the potential clinical outcomes, a probability of being indicated by the patient data, to select, based on the probabilities, one or more anamnestic question from set of pre-configured anamnestic questions stored in a database, to output the one or more selected anamnestic questions to a user via the user interface, to receive one or more answers to the one or more selected anamnestic questions from the user via the user interface, and to adapt the probabilities based upon the answers.

According to another embodiment, the invention further relates to an reading system comprising the system for clinical decision support and a medical information system configured to acquire, store and/or forward patient data (comprising the patient data of the target patient and reference patient data sets of one or more reference patients to be compared with the target patient). Thereby, the interface unit is further configured to receive the patient data from the medical information system.

According to another embodiment, the present invention is directed to a computer program product comprising program elements which induce a computing unit of a system for clinical decision support to perform the steps according to the above method, when the program elements are loaded into a memory of the computing unit.

According to another embodiment, the present invention is directed to a computer-readable medium on which program elements are stored that are readable and executable by a computing unit of a system for clinical decision support, in order to perform steps of the inventive method, when the program elements are executed by the computing unit.

According to another embodiment, the present invention is directed to a computer-implemented method for clinical decision support, the method comprising:

receiving patient data of a target patient;

determining, based on the patient data, a number of potential clinical outcomes associated with the target patient;

calculating, for each respective potential clinical outcome of the number of potential clinical outcomes, a respective probability of being indicated by the patient data, thereby calculating a plurality of probabilities;

selecting, based on the plurality of probabilities calculated, one or more anamnestic questions from a set of anamnestic questions stored in a database;

presenting the one or more anamnestic questions selected to a user via a user interface;

receiving one or more answers to the one or more anamnestic questions selected, from the user via the user interface; and adapting the plurality of probabilities based upon the one or more answers received.

According to another embodiment, the present invention is directed to a system for clinical decision support, the system comprising an interface, configured to interface with a user of the system and a database storing a set of pre-configured anamnestic questions and configured to receive patient data of a target patient; and a computing unit configured to:

determine, based on the patient data, a number of potential clinical outcomes for the target patient;

calculate, for each of the number of potential clinical outcomes, a respective probability of being indicated by the patient data, and thereby calculate a plurality of probabilities;

select, based on the plurality of probabilities, one or more anamnestic question from a set of pre-configured anamnestic questions stored in the database;

present the one or more selected anamnestic questions to a user via the interface;

receive one or more answers to the one or more anamnestic questions selected, via the interface; and adapt the plurality of probabilities based upon the one or more answers received.

According to another embodiment, the present invention is directed to a system for clinical decision support, the system comprising an interface, configured to interface with a user of the system and a database storing a set of pre-configured anamnestic questions and configured to receive patient data of a target patient; and at least one processor configured to:

determine, based on the patient data, a number of potential clinical outcomes for the target patient;

calculate, for each of the number of potential clinical outcomes, a respective probability of being indicated by the patient data, and thereby calculate a plurality of probabilities;

select, based on the plurality of probabilities, one or more anamnestic question from a set of pre-configured anamnestic questions stored in the database;

present the one or more selected anamnestic questions to a user via the interface;

receive one or more answers to the one or more anamnestic questions selected, via the interface; and adapt the plurality of probabilities based upon the one or more answers received.

According to another embodiment, the present invention is directed to a non-transitory computer program product storing program elements which induce at least one processor of a system for clinical decision support to perform the method of an embodiment, when the program elements are loaded into a memory of the system and executed by the at least one processor.

According to another embodiment, the present invention is directed to a non-transitory computer-readable medium storing program elements, readable and executable by at least one processor of a system for clinical decision support, to perform the method of an embodiment when the program elements are executed by the at least one processor.

BRIEF DESCRIPTION OF THE DRAWINGS

Characteristics, features and advantages of the above described invention, as well as the manner they are achieved, become clearer and more understandable in the light of the following description and embodiments, which will be described in detail with respect to the figures. This following description does not limit the invention on the contained embodiments. Same components or parts can be labeled with the same reference signs in different figures. In general, the figures are not drawn to scale. In the following.

DETAILED DESCRIPTION OF THE EXAMPLE EMBODIMENTS

Figure 1:
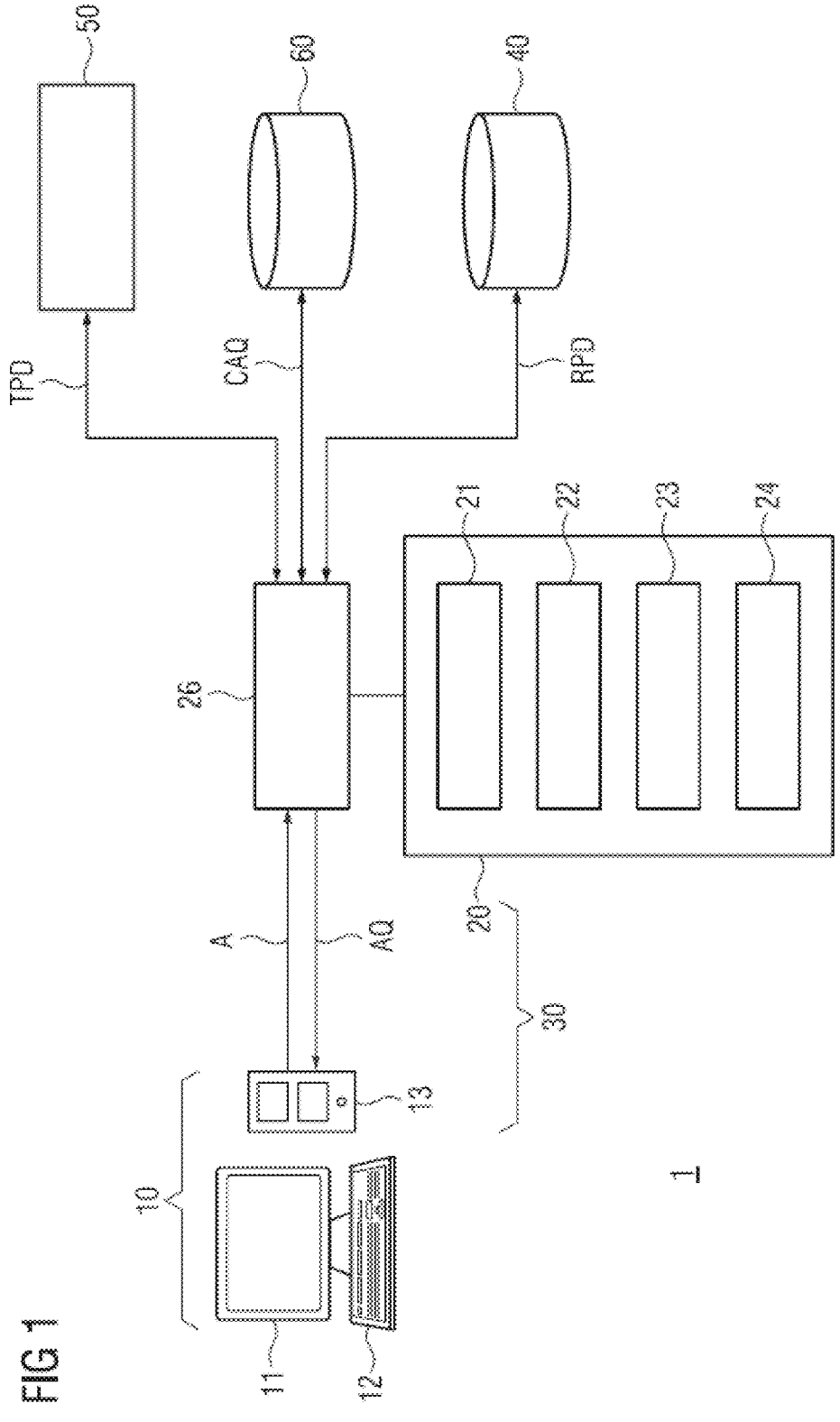
FIG. 1 depicts a clinical decision support system according to an embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to an embodiment, a computer-implemented method for clinical decision support is provided. The method comprises a plurality of steps. A first step is directed to receiving patient data of a target patient. A further step is directed to determining a number of potential clinical outcomes associated with the target patient based on the patient data. A further step is directed to calculating, for each of the potential clinical outcomes, a probability of being indicated by the patient data. A further step is directed to selecting, as a function of the probabilities, one or more anamnestic questions from a set of pre-configured anamnestic questions stored in a database. A further step is directed to presenting the one or more selected anamnestic questions to a user via a user interface. A further step is directed to receiving one or more answers (or responses) to the one or more selected anamnestic questions from the user via the user interface. And yet a further step is directed to adapting the probabilities based upon the answers.

In other words, an embodiment of a computer-implemented method for providing one or more probabilities for one or more potential clinical outcomes for a target patient is provided. The method comprises a plurality of steps. A first step is directed to receiving patient data of a target patient. A further step is directed to determining a number of potential clinical outcomes associated with the target patient based on the patient data. A further step is directed to calculating, for each of the potential clinical outcomes, a probability of being indicated by the patient data. A further step is directed to selecting, as a function of the probabilities, one or more anamnestic questions from a set of pre-configured anamnestic questions stored in a database. A further step is directed to presenting the one or more selected anamnestic questions to a user via a user interface. A further step is directed to receiving one or more answers (or responses) to the one or more selected anamnestic questions from the user via the user interface. A further step is directed to adapting the probabilities based upon the answers. And yet a further step is directed to providing the adapted probabilities.

According to the above embodiment, the target patient may be seen as the patient currently under consideration by a user. The user may be a healthcare professional such as physician, technical assistant, nurse, radiologist, pathologist and so forth. 'Under consideration' may mean that one or more clinical decisions are to be made for the target patient. According to some examples, the decisions may comprise treatment decisions or clinical diagnoses. Further, the decisions may relate to a prognosis for the patient's case or to further actions such as referrals or the enrolment in clinical trials.

The clinical decisions shall be made based on the patient data. In general, the patient data comprises any information which could be helpful in the underlying task of coming to an appropriate clinical decision. As such, the patient data may comprise personal details of the target patient (such as age, gender, habits, insurance details, etc.). Further, the patient data may comprise the health record of the target patient, e.g., in the form of an electronic medical record (EMR). In addition, the patient data may comprise electronic reports from previous examinations comprising one or more previous findings, prognoses, actions taken, and other clinical decisions. Moreover, the patient data may comprise data which has been measured in one or more medical examinations, which may comprise non-image data and image data. The non-image data may be lab data, such as gene sequences obtained from a biopsy sample, blood values, cardiovascular values and so forth. The image data may be radiology image data. The radiology image data may relate to two-dimensional image data providing two dimensions in space. Further, the radiology image data may relate to three-dimensional image data providing three dimensions in space. In general, the radiology image data depicts a body part of a patient in the sense that it contains two- or three-dimensional image data of the patient's body part. The radiology image data may, for example, be in the form of an array of pixels or voxels. Such arrays of pixels or voxels may be representative of intensity, absorption or other parameter as a function of three-dimensional position, and may, for example, be obtained by suitable processing of measurement signals obtained by a medical imaging modality. A medical imaging modality corresponds to a system used to generate or produce medical images. For example, a medical imaging modality may be a computed tomography system (CT system), a magnetic resonance system (MR system), an angiography (or C-arm X-ray) system, a positron-emission tomography system (PET system) or the like. Besides radiology image data, the patient data may comprise digital pathology image data such as histopathology images acquired with a digital pathology slide scanner. Histopathology images may relate to slices from biopsy samples of the target patient which have been stained with one or more pigments. The most commonly used stain in histopathology is a combination of hematoxylin and eosin (often abbreviated H&E). Other compounds used to color tissue sections include safranin, Oil Red O, congo red, silver salts and artificial dyes. Recently, also antibodies are used for specifically identifying categories of cells in digital pathology images.

The patient data may be received from an healthcare information system comprising one or more databases and servers. The healthcare information system may be a local system within the premises of a healthcare organization. Moreover, the healthcare information system may be cloud based. The healthcare informatics system may comprise one or more standardized components such as a picture archiving and communication system (PACS), a radiology information system (RIS), a laboratory information system (LIS), a hospital information system (HIS), or an electronic medical record system (EMR). Image data comprised in the patient data may be formatted according to the DICOM format. DICOM (=Digital Imaging and Communications in Medicine) is an open standard for the communication and management of medical imaging information and related data in healthcare informatics. DICOM may be used for storing and transmitting medical images and associated information enabling the integration of medical imaging devices such as scanners, servers, workstations, printers, network hardware, and picture archiving and communication systems (PACS). It is widely adopted by clinical syndicates, hospitals, as well as for smaller applications like doctors' offices or practices. A DICOM data object consists of a number of attributes, including items such as patient's name, ID, etc., and also special attributes containing the image pixel data and metadata extracted from the image data. For describing data formats and exchanging electronic health records, corresponding standards may be relied upon such as the HL7 FHIR standard. Further, besides designated databases, the healthcare informatics system may directly involve medical imaging modalities such as radiology and/or pathology imaging systems.

"Receiving" in the framework of the application may mean that the patient data is acquired from the healthcare information system. That is, the patient data may be directly acquired from the medical imaging modalities or from appropriate databases such as the aforementioned picture archiving and communication system (PACS) or any other suitable medical image storing facility. Thereby, the resources of the healthcare information system may be queried separately, e.g., based upon the target patient's ID or other suitable identifier. Moreover, a concerted query may be sent to the healthcare information system which may be configured to manage such data requests internally.

Based on the received patient data, a number of potential clinical outcomes is determined. A clinical outcome can be perceived as a medical result, statement, assertion, or conclusion which can be derived from the patient data. As such any clinical outcome may be regarded as contributing to a clinical decision. Accordingly, the automatic determination of clinical outcomes contributes to the clinical decision making and assists the user in drawing the right conclusion from the patient data. The potential clinical outcomes thereby may be seen as a selection of results which come into question based on the patient data. According to some examples, the potential clinical outcomes respectively indicate a disease name.

The determination of the clinical outcomes based on the patient data may involve extracting information from the patient data. This information may then be compared to clinical guidelines cockpits, electronic textbooks (such as the Thieme eRef), or decision trees or matched with clinical ontologies. Extracting information may include applying one or more trained functions to the patient data which are trained to identify relevant pieces of information in the patient data. For instance, a natural language processing (NLP) based trained algorithm may be used to mine electronic reports comprised in the patient data for prior diagnoses—which naturally come into question for a re-examination of the case. Moreover, the information extracted from the patient data may be compared to distribution data representing the distribution of one or more clinical outcomes for a population of patients against a given sample space.

Besides the mere mentioning of potential clinical outcomes, the method foresees to also provide indications for their respective likelihood or confidence of being actually attributable to the target patient based on the patient data. To this, end a probability is calculated for each clinical outcome which is a measure for the likelihood that a given clinical outcome is indicated by the patient data. Like the determination of the clinical outcomes as such, the calculation of the corresponding probabilities is based on the patient data. Specifically, relevant information may be extracted from the patient data and compared to or matched with clinical guidelines, cockpits, electronic textbooks, clinical decision trees, clinical ontologies, or the aforementioned distribution data. In this regard, the aforementioned trained functions may be configured (trained) to provide the probabilities as yet a further output if applied to the patient data.

Trained functions, in general, may be seen as mapping input data to output data thereby fulfilling a certain learned task (in this case: determining a set of potential clinical outcomes from the patient data and estimating the corresponding probabilities). The relation between input and output may be governed by one or more (in general: a plethora) of parameters embedded in the trained functions. The values of the parameters may be learned (adapted) during training according to the task, the trained function will have to fulfill. Other terms for trained function may be trained mapping specification, mapping specification with trained parameters, function with trained parameters, trained machine learned model, algorithm based on artificial intelligence, or machine learned algorithm. Applying trained functions may mean inputting the patient data into the trained function.

Once the potential clinical outcomes and the associated probabilities have been determined for the target patient's case, this information is used to select a number of anamnestic questions to be shown to the user. Being based on the probabilities and, optionally, the clinical outcomes and/or the patient data, the selected anamnestic questions are specifically tailored to the case for which a clinical decision is to be made. It is an idea of the invention to choose the anamnestic question(s) such that the corresponding answers would clarify which of the retrieved potential clinical outcomes are relevant for the target patient and which are less important. As such, the selected anamnestic questions are selected such that the answers to these questions will affect the probabilities. The anamnestic questions thus may concern any information which is not contained or directly derivable from the patient data. Accordingly, the anamnestic questions may ask for additional personal information, risk factors, the medical history, etc. of the target patient. According to some examples, only one anamnestic question is selected—which would be the one having the greatest impact on the probabilities (or which would reduce the uncertainty the most). According to other examples, more than one anamnestic question is selected.

According to some examples, the anamnestic question(s) are automatically picked from a set of pre-configured anamnestic questions as stored in a database. The preconfigured version may be stored in the database in electronic format such as in the form of text strings. The database (also denoted as 'query database' in the following) may be a local database such as a non-volatile memory of a computing system running a program executing the method steps according to the above embodiment. Moreover, the database may be an online database in a cloud or located at a local server. According to some examples, pre-configured may mean that the set of anamnestic questions in the database is generated beforehand. In other words, the set of anamnestic questions may be seen as a compendium of questions which, as such, is independent of the individual case currently reviewed. The generation process of the set of anamnestic questions may be achieved by statistically analyzing common symptoms, lab results or findings from reports regarding specific diseases. Also, getting expert opinions to collect questions is another feasible option. Another option would be consulting textbooks and/or clinical guidelines or cockpits. Thus, according to some examples, the set of pre-configured anamnestic questions has been derived empirically.

'Based on the probabilities' or 'as a function of the probabilities' in the context of the selection of the number of anamnestic questions may mean that the distribution of the calculated probabilities and the projected influence of the hypothetical answers to the selected anamnestic questions on this distribution are analyzed. To this end, one or more statistical properties of the distribution of the probabilities and their anticipated hypothetical change with the knowledge gain through the answers may be evaluated. These statistical properties may by at least one of the entropy, variance, skewness, kurtosis and so forth. Self-speaking, also the patient data and/or the clinical outcomes as such may be taken into account for finding the right anamnestic questions to ask. In particular, prior or similar cases may be considered where one or the other anamnestic question has been recorded as useful for narrowing down the set of potential clinical outcomes. In addition to that or as an alternative, online textbooks, clinical guidelines, or cockpits may be considered which may suggest certain questions in order to verify or rule out certain clinical outcomes.

Once one or more suited anamnestic questions have been selected, they are presented to the user via a user interface. According to some examples, only the most relevant question may be presented. According to other examples, a sub-set or all of the selected questions may be presented. The user interface may be a graphical user interface within which the questions are displayed. Thereby, if more than one anamnestic question has been selected, the questions may be presented one at a time or all at once. Further, the anamnestic questions may be read to the user via a loudspeaker using a text-to-speech interface.

The user interface may be further configured to collect the answers of the user to the anamnestic questions. For instance, the user may enter his answers in a graphical user interface, e.g., by activating check boxes associated to the displayed anamnestic questions or by entering written text using, e.g., a keyboard or touch-sensitive screen. In addition or as an alternative, the user may provide his answers via a speech recognition module which transfers spoken answers into information suited for further processing by the method.

Finally, in a next step, the answers provided by the user are evaluated and used to adapt the probabilities that the respective clinical outcome is indicated by the patient data. For instance, certain information as provided by an answer to an anamnestic question may render a specific clinical outcome considerably more likely while others become less relevant. Therefore, the adaptation of the probabilities reflects the information gain through the anamnestic questions and helps to sharpen the clinical picture of the target patient's case—which improves the basis for clinical decision making for the user.

The adapted probabilities may be provided to a user, e.g., via the above user interface, e.g., in the form of a graphical user interface displayed on the user interface. The probabilities may be displayed directly or indirectly. Directly may mean that the probabilities are shown as such. Indirectly may mean that the adapted probabilities are used for deriving an appropriate graphical representation, such as a ranking of the associated clinical outcomes. Further "providing" in this context may mean archiving the adapted probabilities in an appropriate database for later use or storing them in a working memory of the system. In addition or as an alternative "providing the adapted probabilities" may mean making the adapted probabilities available for a user or any subsequent method steps/computer-implemented modules directed to a utilization of the adapted probabilities.

The method steps as introduced above synergistically contribute to a method facilitating an efficient and robust clinical decision support for a user. Not only does the method automatically retrieve possible clinical outcomes for a target patient's case, it also provides a concept for further narrowing down the potential clinical outcomes. This is achieved by automatically selecting and asking informative questions to a user (i.e., the clinician/physician/technician who is to make a clinical decision for the target patient). The information gain from the user's answers is used to successively increase the confidence of the outcome and rule out differential results. The method thus serves the technical purpose of providing a clinical outcome (which may be, e.g., a medical diagnosis) by an automated system or method processing patient data (which may comprise physiological measurements). This is achieved by way of a continued and/or guided human-machine interaction process involving automatically selected questions and processing the user's answers. As such, the result of the method is neither static nor predetermined. Rather, it is adapted to the target patient's case and the user's input. Accordingly, the method is capable of providing more accurate and reliable outcome in order to better support the user in providing clinical decisions.

Summarizing the above, the method, in other words, first identifies possible clinical outcomes (which may be, according to some examples, disease candidates) for the target patient. To this end, the method uses the available patient data associated to the target patient. Then, the method calculates a predictive information gain for a set of anamnestic questions according to the identified clinical outcome. The method then asks the most informative anamnestic question(s) to the user by speech or visual interface. If the answer is informative, the methods re-ranks the potential clinical outcomes according to the answer(s). After re-ranking, some of the unlikely clinical outcomes may be eliminated.

According to an embodiment, the patient data includes: radiology image data depicting a body part of the target patient, and/or pathology image data depicting at least a part of sample taken from the target patient, and/or non-image patient data of the target patient.

With the above data sets, a holistic picture of the health-care data of the target patient can be provided. With that, it can be ensured that all available information is adequately considered. The pathology image data may relate to a sample extracted by a biopsy procedure. In particular, the pathology images may comprise one or more histopathology images. Moreover, the pathology image data may relate to macroscopic pathology images showing photographs of extracted tumor tissue or entire body parts of the target patient. The radiology image data may have been acquired with the abovementioned imaging modalities such as MR-, CT-, PET-, or X-Ray-systems and the like. The non-image data may comprise lab-data, personal patient information, the electronic medical record of the target patient, structured or unstructured medical reports, digital referral letters and so forth.

According to an embodiment, the clinical outcomes respectively include one or more statements which are of relevance for diagnosing the target patient, and/or for making therapy decisions for the target patient and/or for making prognoses for the target patient's health state and/or for defining further actions for the target patient.

In other words, the clinical outcomes are (actionable) results derivable form the gross information available for the target patient. This information may include the patient data as such, but also information about similar cases, textbook knowledge, online resources, clinical guidelines and cock-pits and the like. Accordingly, the clinical outcomes may be propositions derivable from a patient's case. In particular, the clinical outcomes may comprise diagnoses (e.g., in the form of one or more disease names), notions of medical abnormalities, suggested treatments, predicted treatment responses, the proposal of one or more clinical trails for the target patient, the eligibility of the target patient for one or more clinical trials, suggestions of a referral to one or more specialist physicians, the prognosis of the target patient's health trajectory (as a function of different treatments, as the case may be), suggestions of further examinations, and so forth. Thus, the clinical outcomes may be seen as contrib-uting factors to one or more clinical decisions to be made by the user for the target patient. By automatically providing a selection of relevant clinical outcomes as introduced above, clinical observations are automatically linked with health knowledge to facilitate a more efficient and complete clini-cal decision-making process.

According to an embodiment, in the step of selecting, the one or more questions are selected according to their respec-tive predictive impact on the probabilities.

This means that the anamnestic questions are not selected arbitrarily but specifically according to their impact on the distribution of probabilities of the identified clinical out-comes. Accordingly, the user is presented with relevant anamnestic question(s) only. 'Relevant' in this context may relate to anamnestic questions which reduce the uncertainty (as expressed by the distribution of probabilities) more than others. Accordingly, the selection of the anamnestic ques-tions may be perceived particularly productive by the user which shortens the decision-making process and increases the acceptance of the assistance method.

According to an embodiment, in the step of selecting, the anamnestic question (currently, i.e., based on the current probabilities) having the highest predictive impact on the probabilities is elected from the set of anamnestic questions.

Accordingly, the attention of the user is focused on only one highly relevant question, which further decreases the burden on the part of the user and may make the method more user-friendly.

According to an embodiment, in the step of selecting, the one or more anamnestic questions are selected based on the distribution of the probabilities and, in particular, based on one or more statistical properties of the distribution of the probabilities.

The statistical properties may be quantifiable properties of a distribution. These may be the entropy, the skewness, the variance and so forth. Basing the selection at least partially on the statistical properties of the distribution of probabili-ties has the advantage that a selection may be made already based on the probabilities without taking into account addi-tional knowledge such as similar cases or clinical guidelines.

According to an embodiment, in the step of selecting, the one or more anamnestic questions are selected based on a predicted change of the probabilities as a function of the sample space of the respective anamnestic question.

The sample space for an anamnestic question is defined by the possible answers to the anamnestic question. If the anamnestic question relates to the gender of the target patient, the answers may be male, female or diverse. Accord-ingly, the sample space would be spanned by male, female, and diverse. If the answer is male, the probabilities may be affected differently than for female or diverse target patients which is reflected in the statistical properties of the under-lying distribution of probabilities. According to some examples, the change in probabilities may conveniently be quantified by evaluating one or more statistical properties of the distribution of probabilities (such as the entropy, the variance, the skewness, etc.)—or the change thereof. Thereby, the different possibilities for answering the anam-nestic question may be factored by an appropriate metric such as by calculating the mean or by using the max-function.

According to an embodiment, the predictive impact is defined as the predictive information gain associated with each anamnestic question, wherein the predictive informa-tion gain for a question Q of the number of anamnestic questions is, in particular, given by:

$$MAX(P(\text{yes})[H(PD|TPD)-H(PD|TPD,Q=\text{yes})],P$$
$$(\text{no})[H(PD|TPD)-H(PD|TPD,Q=\text{no})])$$

with:
  $H(PD|TPD)$ being the initial entropy H of the probability distribution PD of the calculated probabilities of the patient data TPD;
  $H(PD|TPD, Q=\text{yes})$ being the entropy H of the probability distribution PD assuming a yes to question Q;
  $H(PD|TPD, Q=\text{no})$ being the entropy H of the probability distribution D assuming a no to question Q;
  $P(\text{yes})$ being the probability for answering question Q with 'yes'; and
  $P(\text{no})$ being the probability for answering question Q with 'no'.

According to the above embodiment, the entropy is used as statistical property of the distribution of probability and the MAX-function is used as the metric for weighting possible answers to question Q. With that, a reliable and reproducible way of identifying relevant anamnestic questions may be defined.

According to an embodiment, the step of selecting one or more anamnestic questions is based on distribution data representing one or more distributions of one or more of the potential clinical outcomes in a population of patients. Thereby, the distribution data optionally represents one or more distributions of one or more of the potential clinical outcomes in a population of patients as a function of one or more sample spaces of one or more anamnestic questions from the set of anamnestic questions.

With the distribution data, the targeted selection of adequate anamnestic questions can be facilitated. If the distribution data, for instance, indicates that a certain clinical outcome is prevalent for a particular age window, the knowledge of the age of the target patient would help to either verify or rule out the clinical outcome. Accordingly, asking the target patient for his age could be a relevant anamnestic question.

According to an embodiment, the step of selecting is based on selection frequencies of the anamnestic questions for prior target patients.

With that, anamnestic questions which have proven particularly useful for prior cases may be kept track of and favored in future selections.

According to an embodiment, the step of selecting is based on one or more clinical guidelines applicable for the target patient.

Clinical guidelines may define a particular course of action dependent on the peculiarities of the case. This course of action may be followed by way of a decision tree, the nodes of which are linked to a clinical outcome and/or anamnestic question concerning the target patient. Basing the selection on one or more clinical guidelines may mean automatically extracting anamnestic questions from a clinical guideline so as to advance in the clinical workflow associated thereto. Accordingly, using clinical guidelines for selecting appropriate questions may contribute to the seamless integration of the method into existing clinical workflows.

According to an embodiment, the method further comprises the step of mining the patient data and/or additional data sources associated with the target patient for finding answers to one or more of the selected anamnestic questions before presenting them to the user.

In other words, the information available for the target patient is automatically searched for answers to the selected anamnestic questions. This may decrease the need to actually ask the selected questions to the user which may make the method faster and more user-friendly.

According to an embodiment, the method further comprises the step of storing the information comprised in the answers of the user in the patient data of the target patient.

Recording the users answers for later use may likewise increase the user-friendliness and efficiency of the method, as this may prevent asking the same questions over and over again.

According to an embodiment, the step of adapting the probabilities is based on distribution data representing one or more distributions of one or more of the potential clinical outcomes in a population of patients, optionally, as a function of one or more sample spaces of one or more anamnestic questions from the set of anamnestic questions.

In particular, adapting the probabilities may mean ranking the target patient in the distribution data in the light of the knowledge gain gathered from the user's answer(s). If, for instance, the answer to the question 'is the target patient a smoker' is affirmative, this may place the target patient at a different spot in the distribution data as compared to if the answer was negative. By consequence, some of the clinical outcomes may become more likely while others remain unaffected or become less likely. In this regard, the distribution data (which may be gathered empirically) may provide an objective measure how to adapt the probabilities as a result of the user's answer(s).

According to an embodiment, each potential clinical outcome is associated with at least one of a plurality of categories (which may be categories of clinical decision making). Likewise, each anamnestic question in the set of anamnestic questions is associated with at least one of the plurality of categories. Then, in the step of selecting, only such questions are considered for being selected, the at least one associated category of which matches at least one of the categories of the potential clinical outcomes.

Categorizing the anamnestic questions according to the categories of the clinical outcome may bring about the advantage that the anamnestic question may be efficiently preselected. According to some examples, the categories may comprise diagnosis, treatment, prognosis or further actions. If a potential clinical outcome pertains to a certain category, only such questions are being considered which are relevant according to the category. Questions which are not relevant at this point are not being considered for selection. Taking 'diagnosis' as an example for the category of a clinical outcome, questions pertaining to future treatment side effects or the health insurance may not have priority. This may be very different, though, if the category of the clinical outcome relates to the eligibility of the target patient to a clinical trial. Accordingly, categorizing clinical outcomes and anamnestic question in a plurality of preconfigured categories may be useful to swiftly select a minimal set of anamnestic question for clarifying the case.

The association of the one or more categories may be performed using an appropriate ontology which maps a particular clinical outcome to a superordinate category. In that sense, the method may further comprise the steps of defining a plurality of categories and associating the potential clinical outcomes and/or the anamnestic questions to one or more of the plurality of categories.

According to an embodiment, at least one category of the plurality of categories is selectable as category selection by the user via the user interface and the method comprises receiving the category selection of the user from the user interface. Thereby, in the step of determining, only such clinical outcomes are considered as potential clinical outcomes the associated category of which matches the category selection of the user.

Usually, for a patient case, a number of different clinical decisions have to made which go into different directions and, thus, may require different considerations. In most cases, a user is only interested in making one particular clinical decision at a time. Other clinical decisions may be not relevant for a particular user or become relevant further downstream of the clinical decision-making process. For instance, a pathologist will typically seek to provide a diagnosis based on histopathology images. He will in most cases not decide about the further therapy of the target patient. Introducing categories for the decision-making task and making these categories selectable by the user thus may deliver a more specific outcome.

According to an embodiment, the steps of selecting one or more anamnestic question, presenting the one or more selected anamnestic questions to a user, receiving one or more answers, and adapting the probabilities based upon the answers, are repeated until at least one of the potential clinical outcomes has a probability above a first predetermined threshold.

In other words, the process of asking anamnestic questions is repeated until at least one of the clinical outcomes has a sufficient confidence level. The threshold may be set automatically or manually by the user.

According to an embodiment, the method further comprises establishing a ranking of the potential clinical outcomes according to their respective probabilities, and displaying the potential clinical outcomes based on the ranking via the user interface.

'Displaying the clinical outcomes' based on the ranking may mean, in particular, that the displaying includes a presentation for the user which is configured such that the ranking may be perceived by the user. This has the technical effect, that the relevance of the clinical outcome can immediately by accessed by the user so that he can use this information in the clinical decision-making process. There is plurality of possibilities of 'how' this information may be conveyed to the user. For instance, the potential clinical outcomes may be arranged in a list ranking the potential clinical outcomes according to the associated probabilities from top to bottom. Another possibility would be directly indicating the probability values in the user interface. As yet another possibility, the potential clinical outcomes may be displayed with numbers indicating their rank. For instance, the most relevant potential clinical outcome (i.e., the one with the highest probability) could be denoted with the number '1', the next relevant one with the number '2' and so forth. Another option involves using a color coding from which the probability can be derived.

After each iteration of the method, the potential clinical outcomes may be re-ranked according to the adapted probabilities and the presentation may be updated accordingly.

According to an embodiment, the method further comprises retrieving auxiliary information associated to the clinical outcomes and displaying the auxiliary information alongside the corresponding potential clinical outcome via the user interface.

The auxiliary information may comprise textbook knowledge taken form an online textbook or guideline, similar case information pertaining to similar cases, distribution data representing the distribution of the potential clinical outcomes in a population of patients as a function of a sample space, links to online textbooks or cockpits, differential clinical outcomes, contact information to specialist clinicians and so forth. For each potential clinical outcome, the auxiliary information may be specifically compiled such that the data presented is adapted according to the underlying potential clinical outcome. With that, the user is provided with relevant additional information making the decision-making process more transparent and explainable. This brings the user in a better position for deciding whether or not to accept the results provided by the method.

According to some examples, the displaying may be configured such that any auxiliary information may be visually assignable to the associated clinical outcome. For instance, the auxiliary information may be visually grouped according to the corresponding clinical outcome. As an example, each clinical outcome may be provided with a box within which the associated auxiliary information is shown.

According to an embodiment, the step of determining a number of potential clinical outcomes comprises: identifying, from a set of reference patients different than the target patient and using the patient data, a number of similar patients, wherein each similar patient has a degree of similarity to the target patient and is associated to at least one known clinical outcome, and compiling the potential clinical outcomes from the known clinical outcomes of the retrieved similar patient data sets.

In other words, the potential clinical outcomes for the target patient are determined based on verified clinical outcomes for similar patients. This may help to decreases the convergence times of the method and yield better results with fewer iterations of questions and answers.

According to an embodiment, the method may further comprise the step of providing a set of reference patients (for the similar patient search). 'Providing' may be in the form of providing a database storing data sets of the reference patients (in the following also denoted as reference patient data sets). The reference patient data sets may generally have the same form as the patient data of the target patient. In particular, the reference patient data sets may comprise image and non-image patient data.

The identification of similar patients amongst the reference patients having a certain degree of similarity with the target patient may be based on a comparison involving the patient data of the target patient and the reference patient data sets. Specifically, according to an embodiment, the step of retrieving a number of similar patients may comprise calculating a data descriptor from the patient data of the target patient, receiving, for each reference patient of the set of reference patients, a corresponding data descriptor; determining, for each reference patient a similarity metric representing the degree of similarity between the data descriptor of the target patient and the data descriptor of the reference patient; and selecting one or more reference patients as similar patients based on the respective similarity metrics.

The corresponding data descriptors may be calculated online upon the similar patient search or may be held available as pre-generated data items stored in the database. In particular, if the patient data of the target patient and reference patient data sets comprise image data, the data descriptors may comprise image feature vectors. For each reference patient taken into account, the similarity metric may represent how similar the reference case is to the target patient. In some examples, the similarity metric may be a distance in vector space between the data descriptor of the target patient and the data descriptors of the reference patients. In other examples, further similarity metrics may be used, such as a cosine similarity between the data descriptors. According to some embodiments, the calculation of the data descriptors from the underlying patient data and/or the identification of similar patients as a whole may be performed by one or more trained functions.

According to an embodiment, the step of calculating, for each of the potential clinical outcomes, a probability of being indicated by the patient data is based on the degrees of similarities.

According to this embodiment, the results of the similar case search are used twofold. On the one hand upon determining the potential clinical outcomes in the first place, and on the other hand upon estimating their associated probabilities of being indicated by the patient data. In this regard, the inventors have recognized that the higher the similarity between two patients, the higher the likelihood that verified clinical outcomes of the similar patient(s) also apply for the target patient. Using this principle, a better starting point for the method can be provided which may improve the accuracy and the perceived reliability of the method.

According to an embodiment, the method further comprises the step of displaying, for all or part of the similar patients, data items (pertaining to the respective similar patient) to the user via the user interface.

According to some examples, the data items may relate to objects comprised in the reference patient data sets which have a high similarity to corresponding objects in the patient data of the target patient. These data items may comprise personal information of the similar patients, distribution data, the healthcare status of the similar patients and so forth. In particular, the data items may relate to medical image data and comprise radiology or digital pathology images.

According to an embodiment, the data items are displayed such that they are visually assignable to the corresponding potential clinical outcome. For instance, the data items may be visually grouped according to the corresponding clinical outcome upon displaying.

According to an embodiment, the method further comprises establishing a ranking of the potential clinical outcomes according to their respective probabilities and displaying the data items based on the ranking.

'Displaying based on the ranking' may mean, in particular, that the visualization is configured such that the ranking may be perceived by the user. By displaying the data items of the similar patients, the user is provided with a holistic picture of the target patient's case, potential clinical outcomes and similar cases with the same outcomes. With that, the user is provided with a comprehensive perception as to why the selected potential clinical outcomes could be relevant. This makes the results of the method readily accessible and contributes to the seamless integration of the method in existing clinical workflows.

According to an embodiment, a system for clinical decision support is provided. The system comprises an interface unit, and a computing unit. The interface unit is configured to interface with a user of the system, a database storing a set of anamnestic questions and to receive patient data of a target patient. The computing unit is configured to determine, based on the patient data, a number of potential clinical outcomes for the target patient, to calculate, for each of the potential clinical outcomes, a probability of being indicated by the patient data, to select, based on the probabilities, one or more anamnestic question from set of pre-configured anamnestic questions stored in a database, to output the one or more selected anamnestic questions to a user via the user interface, to receive one or more answers to the one or more selected anamnestic questions from the user via the user interface, and to adapt the probabilities based upon the answers.

According to an embodiment, the system is adapted to implement an embodiment of the inventive method of providing clinical decision support to a user.

The computing unit may be realized as a data processing system or as a part of a data processing system. Such a data processing system can, for example, comprise a cloud-computing system, a computer network, a computer, a tablet computer, a smartphone and/or the like. The computing unit can comprise hardware and/or software. The hardware can comprise, for example, one or more processors, one or more memories and combinations thereof. The one or more memories may store instructions for carrying out the method steps according to the invention. The hardware can be configurable by the software and/or be operable by the software. Generally, all units, sub-units or modules may at least temporarily be in data exchange with each other, e.g., via a network connection or respective interfaces. Consequently, individual units may be located apart from each other.

The interface unit may comprise an interface for data exchange with a local server or a central web server via internet connection for receiving the patient data of the target patient. The interface unit may be further adapted to interface with one or more users of the system via a user interface, e.g., by displaying the selected anamnestic questions to the user (e.g., in a graphical user interface) and/or by allowing the user to input the corresponding answers.

According to an embodiment, the system further comprises the database (or query database) storing the set of pre-configured anamnestic questions.

According to another embodiment, the invention further relates to an reading system comprising the system for clinical decision support and a medical information system configured to acquire, store and/or forward patient data (comprising the patient data of the target patient and reference patient data sets of one or more reference patients to be compared with the target patient). Thereby, the interface unit is further configured to receive the patient data from the medical information system.

According to an embodiment, the medical information system comprises one or more archive stations for storing patient data, which may be realized as a cloud storage or as a local or spread storage, e.g., as a PACS (Picture Archiving and Communication System) or EHR (Electronic Health Record). Further, the medical information system may comprise one or more medical data generation modalities, such as medical imaging modalities comprising a computed tomography system, a magnetic resonance system, an angiography (or C-arm X-ray) system, a positron-emission tomography system, a mammography system, and/or a system for acquiring digital pathology images or the like.

According to another embodiment, the present invention is directed to a computer program product comprising program elements which induce a computing unit of a system for clinical decision support to perform the steps according to the above method, when the program elements are loaded into a memory of the computing unit.

According to another embodiment, the present invention is directed to a computer-readable medium on which program elements are stored that are readable and executable by a computing unit of a system for clinical decision support, in order to perform steps of the inventive method, when the program elements are executed by the computing unit.

The realization of the invention by a computer program product and/or a computer-readable medium has the advantage that already existing providing systems can be easily adopted by software updates in order to work as proposed by the invention.

The computer program product can be, for example, a computer program or comprise another element next to the computer program as such. This other element can be hardware, e.g., a memory device, on which the computer program is stored, a hardware key for using the computer program and the like, and/or software, e.g., a documentation or a software key for using the computer program. The computer program product may further comprise development material, a runtime system and/or databases or libraries. The computer program product may be distributed among several computer instances.

FIG. 1 depicts a system 1 for supporting a user upon making one or more clinical decision for a patient currently under review. Subsequently, the patient currently under review may also be denoted as 'target patient'. To each target patient data TPD is associated which may be used by system 1 and/or its user within the subsequently described clinical decision-making process. In this regard, system 1 is adapted to perform the method according to one or more embodiments, e.g., as further described with reference to FIGS. 2 to 9. The clinical decision support according to some embodiments comprises associating one or more potential clinical outcomes or statements or assertions to the target patient based on the available patient data, automatically asking informative questions to a user of system 1 about the target patient's case, and, optionally, auxiliary information, e.g., relating to similar cases or distribution data. The potential clinical outcomes may be seen as automatically retrieved results contributing to one or more clinical decision for the target patient. A user, according to some examples, may generally relate to a healthcare professional such as a physician, clinician, technician, radiologist, pathologist and so forth. According to some examples, the group of users explicitly does not involve the target patient.

System 1 comprises a user interface 10 (as part of the interface unit) and a processing system 20 (as part of the computing unit). Further, system 1 may comprise a similar case database 40 for storing a plurality of reference patient data sets RPD, a query database 60 for storing a set of pre-configured anamnestic questions CAQ, and a medical information system 50 for acquiring, storing and/or forwarding patient data TPD, RPD. According to some examples, query database 60 and/or similar case database 40 may be part of medical information system 50. Alternatively, query database 60 may be a embodied by a non-volatile memory within processing system 20. Moreover, query database 60 may be an online repository or a local database within system 1.

The anamnestic questions CAQ stored in query database (also denoted as 'set of anamnestic questions') may be seen as a pool of candidate anamnestic questions CAQ from which one or more anamnestic questions AQ particularly relevant for the target patient may be selected. The anamnestic questions CQA in query database 60 may be pre-configured based on an empirical evaluation of reference patient cases. Specifically, candidate anamnestic questions CQA may be derived by statistically analyzing common symptoms, labs results, or findings from reports regarding specific diseases. In addition or as an alternative, evaluating expert opinions on reference patient cases is yet another option to identify candidate anamnestic questions CQA.

The patient data TPD of the target patient as well as the reference patient data sets RPD may comprise image and/or non-image data. Image data may relate to three-dimensional image data sets acquired, for instance, using a computed tomography system or a magnetic resonance imaging system. Further, image data may relate to two-dimensional medical images, for instance, acquired with an X-Ray facility. In general, any imaging modalities and scanners may be used, such as ultrasound, x-ray, angiography, fluoroscopy, positron emission tomography, single photon emission computed tomography, or others. Suchlike image data may also be referred to as radiology image data. Generally, radiology image data may show a body part of a patient. The body part depicted will comprise various anatomies and organs. Considering the chest area as body part, the image data might, for instance, depict the lung lobes, the rib cage, the heart, lymph nodes, and so forth. Another example for medical image data comprised in the patient data are digital pathology images. Digital pathology images may be acquired using a digital pathology imaging system such as a slide scanner. Digital pathology images show tissue slices, e.g., prepared from a biopsy sample of a patient which may be stained with appropriate markers.

Image data comprised in patient data TPD or reference patient data sets RPD may be formatted according to the DICOM format. DICOM (=Digital Imaging and Communications in Medicine) is an open standard for the communication and management of medical imaging information and related data in healthcare informatics. DICOM may be used for storing and transmitting medical images and associated information enabling the integration of medical imaging devices such as scanners, servers, workstations, printers, network hardware, and picture archiving and communication systems (PACS). It is widely adopted by clinical syndicates, hospitals, as well as for smaller applications like doctors' offices or practices. A DICOM data object consists of a number of attributes, including items such as patient's name, ID, etc., and also special attributes containing the image pixel data and metadata extracted from the image data.

Besides image data, patient data TPD and reference patient data sets RPD may contain non-image data. Non-image data may relate to non-image examination results such as lab data, vital signs records (comprising, e.g., ECG data, blood pressure values, ventilation parameters, oxygen saturation levels) and so forth. Moreover, non-image data comprise structured and unstructured reports relating to prior examinations of the patient. Further, non-image data may comprise personal information of the patient such as gender, age, weight, insurance details, and so forth.

User interface 10 comprises a display unit 11 and an input unit 12. User interface 10 may be embodied by a mobile device such as a smartphone or tablet computer. Further, user interface 10 may be embodied as a workstation in the form of a desktop PC or laptop. Input unit 12 may be integrated in display unit 11, e.g., in the form of a touch screen. As an alternative or in addition to that, input unit 12 may comprise a keyboard, a mouse or a digital pen and any combination thereof. Display unit 11 is configured for displaying information about the target patient based on the patient data TPD, the selected anamnestic questions AQ, the potential clinical outcomes O1, O2, O3, . . . , ON (O1 . . . ON in the following) derived from the patient data TPD and the answers A of the user, and any auxiliary information associated to the potential clinical outcomes O1 . . . ON. User interface 10 is further configured to receive the answers A provided by the user to the anamnestic questions AQ presented.

User interface 10 further comprises an interface computing unit 13 configured to execute at least one software component for serving display unit 11 and input unit 12 in order to provide a graphical user interface (c.f. FIGS. 6 to 9) for allowing the user to select a target patient's case to be reviewed. In addition, interface computing unit 13 may be configured to communicate with medical information system 50 or processing system 20 for receiving the patient data TPD of the target patient and/or the result of clinical decision support procedure. The user may activate the software component via user interface 10 and may acquire the software component, e.g., by downloading it from an internet application store. According to an example, the software component may also be a client-server computer program in the form of a web application running in a web browser. The interface computing unit 13 may be a general processor, central processing unit, control processor, graphics processing unit, digital signal processor, three-dimensional rendering processor, image processor, application specific integrated circuit, field programmable gate array, digital circuit, analog circuit, combinations thereof, or other now known device for processing image data.

Similar case database 40 is configured to store a number of reference patient data sets RPD. Reference patient data sets RPD relate to reference cases with known or verified clinical outcomes. The reference patient data sets RPD may have the same form as the patient data TPD of the case currently under review. In particular, reference patient data sets RPD may each comprise image data and non-image data.

Processing system 20 may comprise sub-units 21-24 configured to process the patient data TPD for finding potential clinical outcomes O1 . . . ON indicated by the target patient and narrowing down this selection by a continuous and guided human-machine interaction.

Processing system 20 may be a processor. The processor may be a general processor, central processing unit, control processor, graphics processing unit, digital signal processor, three-dimensional rendering processor, image processor, application specific integrated circuit, field programmable gate array, digital circuit, analog circuit, combinations thereof, or other now known device for processing image data. The processor may be single device or multiple devices operating in serial, parallel, or separately. The processor may be a main processor of a computer, such as a laptop or desktop computer, or may be a processor for handling some tasks in a larger system, such as in the medical information system or the server. The processor is configured by instructions, design, hardware, and/or software to perform the steps discussed herein. Alternatively, processing system 20 may comprise a real or virtual group of computers like a so called 'cluster' or 'cloud'. Such server system may be a central server, e.g., a cloud server, or a local server, e.g., located on a hospital or radiology site. Further, processing system 20 may comprise a memory such as a RAM for temporally loading the patient data TPD and/or the anamnestic question AQ to be asked to the user for narrowing the selection of potential clinical outcomes O1 . . . ON. Alternatively, such memory may as well be comprised in user interface 10. Additionally, processing system 20 may comprise similar case database 40 and/or query database 60 in a local storage.

Sub-unit 21 is a similar case retrieval module or unit. It is configured to access similar case database 40 and retrieve one or more reference cases therefrom which have a certain degree of similarity to the case at hand. To this end, sub-unit 21 may be configured to generate a data descriptor (or feature vector or feature signature) from the patient data TPD of the target patient. The data descriptor may be seen as a data vector in which all relevant information for the ensuing comparison to the reference cases is encoded. Relevant information may be extracted from non-image data as well as image data comprised in the patient data TPD. Relevant information extracted from non-image data may, for instance relate to personal information of the patient (such as age or gender), lab values (such as the PSA value), and/or vital signs records. Relevant information derived from image data may, for instance, relate to image features (such as image patterns, location and size of lesions, etc.). To extract the data descriptor, sub-unit 21 may be configured to run a trained function which has been trained to extract a data descriptor from the patient data TPD. Once the data descriptor has been generated from the patient data TPD, sub-unit 21 compares it to corresponding data descriptors extracted from the reference patient data sets RPD as stored in the similar case database 40. Reference cases with data descriptors having certain degree of similarity with the data descriptor extracted for the target patient may then be identified as 'similar cases' for the target patient.

Sub-unit 22 is a clinical outcome prediction module or unit. Sub-unit 22 is configured to associate a number of potential clinical outcomes O1 . . . ON to the target patient. Further, sub-unit 22 is configured to derive probabilities PO1, PO2, PO3, . . . , PON (abbreviated as PO1 . . . PON in the following) for each potential clinical outcome O1 . . . ON. Thereby probabilities PO1 . . . PON indicate for each potential clinical outcome O1 . . . ON the likelihood of being indicated by the patient data TPD of the target patient. As mentioned, a clinical outcome O1 . . . ON, in general, may relate to any result the examination of a patient case might have. According to some examples, clinical outcomes O1 . . . ON may be classified in the following four categories: diagnosis, therapy, prognosis, and further actions. Sub-unit 22 may be configured to derive potential clinical outcomes O1 . . . ON and associated probabilities PO1 . . . PON from the similar cases identified by sub-unit 21. This follows the insight that a clinical outcome which proved relevant for similar cases is likely to be relevant for the case currently under review as well. Quantitatively, the aforementioned probabilities PO1 . . . PON may be derived from the degrees of similarity (as will be further detailed below). In addition or as an alternative, sub-unit 22 may be configured to derive one or more potential clinical outcomes O1 . . . ON by comparing the patient data TPD to empirical data. This empirical data may be provided in the form of distribution data of clinical outcomes across a cohort of patients as a function of one or more key values of the patient (such as age, gender, etc.). Further such empirical data may comprise online textbooks or knowledge databases. In this regard, according to some examples, the same data descriptor as described in connection with the similar case search may also be used for the comparison to empirical data. In any case, sub-unit 22 will provide a selection of potential clinical outcomes O1 . . . ON with corresponding probabilities PO1 . . . PON of being relevant for the target patient. This selection may be preliminary and broad as it may include only marginally relevant or even conflicting clinical outcomes O1 . . . ON.

Sub-unit 23 is a query module or unit configured to concretize the selection of clinical outcomes O1 . . . ON as identified by sub-unit 22. To do so, sub-unit 23 is configured to analyze the probabilities PO1 . . . PON associated with the retrieved clinical outcomes O1 . . . ON and select anamnestic questions AQ the answers of which are suited to increase the certainty in the assignment of the potential clinical outcomes O1 . . . ON to the target patient. In a way, sub-unit 23 may be seen as being configured to determine 'unknowns' in connection with the target patient the knowledge of which could improve the assignment of the potential clinical outcomes O1 . . . ON. The anamnestic questions AQ may be selected form the query database 60. As will be further detailed below, the candidate anamnestic questions CAQ comprised in query database 60 may be evaluated according to the potential impact the corresponding answers would have for the probabilities PO1 . . . PON. To decrease the computational costs, the candidate anamnestic questions CAQ may be categorized according to the type of patient data TPD that is being analyzed (radiology data does entail different questions as compared to digital pathology data) or according to the kind of clinical outcome O1 . . . ON that is being looked at (providing a diagnosis selection might require different additional knowledge than determining whether a patient is eligible for a clinical trial). Sub-unit 23 may then be configured to only consider candidate anamnestic questions CAQ of a certain category matching the patient data TPD and/or the category of the intended clinical decision support. In order to select meaningful anamnestic questions AQ, sub-unit 23 may rely on distribution data showing the distribution of the clinical outcomes O1 . . . ON under considerations for a population of patients as a function of a given parameter. If, for instance, a distribution indicates that a certain therapy side effect has a prevalence for patients of a certain age, asking for the age of the patient could clarify whether or not the side effect is to be expected. Once one or more anamnestic questions AQ have been selected, sub-unit 23 may further be configured to mine the patient data TPD for already existing information that would answer one or more of the selected anamnestic questions AQ. In this regard, sub-unit 23 may further be configured to actively query additional data sources such as the electronic health record of the patient.

Sub-unit 23 is further configured to induce the user interface 10 to display the selected anamnestic questions AQ to the user and to collect the user answers via the user interface 10. In addition, sub-unit 23 is configured to process the users answers A and calculate how the answers A affect the probabilities PO1 . . . PON associated to the clinical outcomes O1 . . . ON. For adapting the probabilities PO1 . . . PON, sub-unit 23 may likewise be configured to evaluate known distribution data of the clinical outcomes O1 . . . ON being considered.

Sub-unit 23 may be configured to undergo the process of selecting anamnestic questions AQ, collecting the answers A and adapting the probabilities PO1 . . . PON repeatedly until a sufficiently high confidence for at least one of the clinical outcomes O1 . . . ON has been reached.

Sub-unit 24, may be conceived as a visualization module, which presents the outcome of the decision support workflow to the user. That is, sub-unit 24 may be configured to rank the clinical outcomes O1 . . . ON according to their corresponding probabilities PO1 . . . PON (initial or adapted). Sub-unit 24 may further be configured to display the clinical outcomes O1 . . . ON according to the ranking, for instance, in the form of a list with decreasing probabilities PO1 . . . PON from top to bottom. Every time the probabilities PO1 . . . PON are adapted, sub-unit 24 may be configured to re-rank the clinical outcomes O1 . . . ON and adapt the presentation accordingly. If the selection of the potential clinical outcomes O1 . . . ON based on a similar case search by sub-unit 22, sub-unit 24 may further be configured to display distinct data items extracted from the reference patient data sets alongside the clinical outcomes O1 . . . ON. According to some examples, the displaying may be such that the data items are visually grouped according to the corresponding clinical outcome O1 . . . ON.

The designation of the distinct sub-units 21-24 is to be construed by way of example and not as limitation. Accordingly, sub-units 21-24 may be integrated to form one single unit (e.g., in the form of "the processor 30") or can be embodied by computer code segments configured to execute the corresponding method steps running on a processor or the like of processing system 20. The same holds true with respect to interface computing unit 13. Each sub-unit 21-24 and interface computing unit 13 may be individually connected to other sub-units and or other components of the system 1 where data exchange is needed to perform the method steps. For example, sub-units 21 and 24 may be connected via an interface 26 to medical information system 50 for retrieving the patient data TPD of the target patient and/or to similar case database 40 for finding similar cases and/or to query database 60 for selecting one or more anamnestic questions AQ from the set of pre-configured anamnestic questions CAQ. Likewise, interface 26 may connect the sub-units 21 to 24 to interface computing unit 13 for forwarding the selected anamnestic questions AQ to the user and collecting the answers A of the user.

Processing system 20 and interface computing unit 13 together may constitute the computing unit 30. Of note, the layout of computing unit 30, i.e., the physical distribution of interface computing unit 13 and sub-units 21-24 is, in principle, arbitrary. For instance, sub-unit 24 (or individual elements of it or specific algorithm sequences) may likewise be localized in user interface 10. The same holds true for the other sub-units 21-23. Specifically, processing system 20 may also be integrated in user interface 10. As already mentioned, processing system 20 may alternatively be embodied as a server system, e.g., a cloud server, or a local server, e.g., located on a hospital or radiology site. According to such implementation, user interface 10 could be designated as "frontend" or "client" facing the user, while processing system 20 could then be conceived as "backend" or server. Communication between user interface 10 and processing system 20 may be carried out using the https-protocol, for instance. The computational power of the system may be distributed between the server and the client (i.e., user interface 10). In a "thin client" system, the majority of the computational capabilities exists at the server. In a "thick client" system, more of the computational capabilities, and possibly data, exist on the client.

Individual components of system 1 may be at least temporarily connected to each other for data transfer and/or exchange. User interface 10 communicates with processing system 20 via interface 26 to exchange, e.g., patient data TPD, data descriptors or the result of the computation. For example, processing system 20 may be activated on a request-base, wherein the request is sent by user interface 10. Further, processing system 20 may communicate with medical information system 50 in order to retrieve a target patient's case. As an alternative or in addition to that, user interface 10 may communicate with medical information system 50 directly. Medical information system 50 may likewise be activated on a request-base, wherein the request is sent by processing system 20 and/or user interface 10. Interface 26 for data exchange may be realized as hardware- or software-interface, e.g., a PCI-bus, USB or fire-wire. Data transfer may be realized using a network connection. The network may be realized as local area network (LAN), e.g., an intranet or a wide area network (WAN). Network connection is preferably wireless, e.g., as wireless LAN (WLAN or Wi-Fi). Further, the network may comprise a combination of different network examples. Interface 26 for data exchange together with the components for interfacing with the user 11, 12 may be regarded as constituting an interface unit of system 1.

Figure 2:
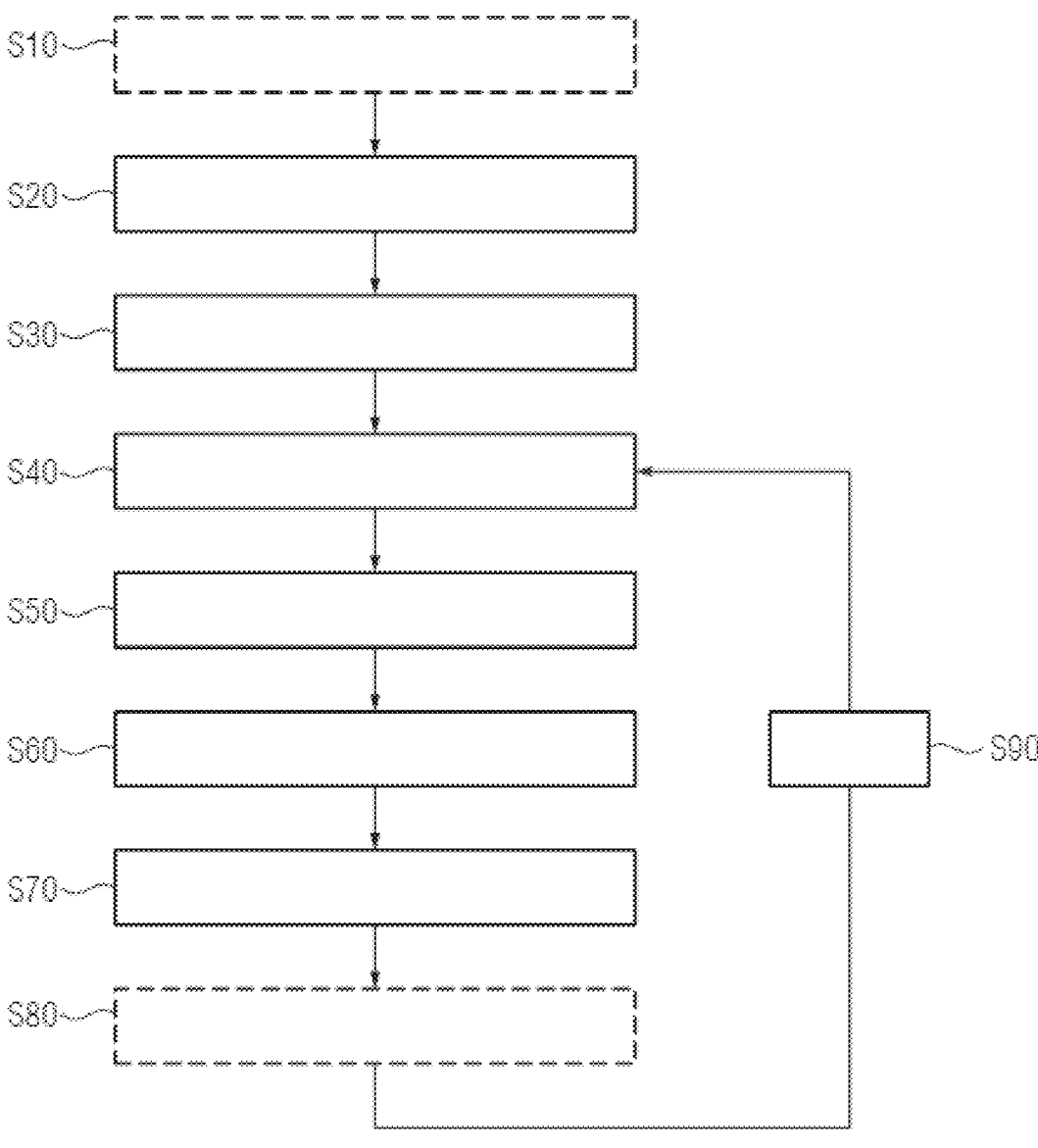
FIG. 2 depicts a flowchart illustrating a computer-implemented clinical decision support method according to an embodiment.

FIG. 2 depicts an inventive method for supporting a user in coming to a clinical decision for the target patient. The order of the steps does not necessarily correspond to the numbering of the steps but may also vary between different embodiments of the present invention. Optional steps are shown with dashed frames in FIG. 2.

In a first step S10, the patient data TPD of the target patient is retrieved. This may involve manually selecting the patient case by the user with the user interface 10 and retrieving the patient data TPD from the medical information system 50. Step S10 may be performed at least partially either on user interface 10 or on processing system 20. Corresponding data exchange is included in this step where necessary.

At subsequent step S20, a number of potential clinical outcomes O1 . . . ON for the target patient is automatically determined based on the patient data TPD. As mentioned, the clinical outcomes O1 . . . ON may in general relate to any actionable result of an examination of a patient case by a physician. Clinical outcomes O1 . . . ON include but are not limited to a medical diagnosis (e.g., by providing one or more disease names), a predicted treatment response, the match of a patient to a clinical trial, the overall prognosis for the patient's health condition and so forth. The number of potential clinical outcomes O1 . . . ON determined may be one or greater than one.

Figure 3:
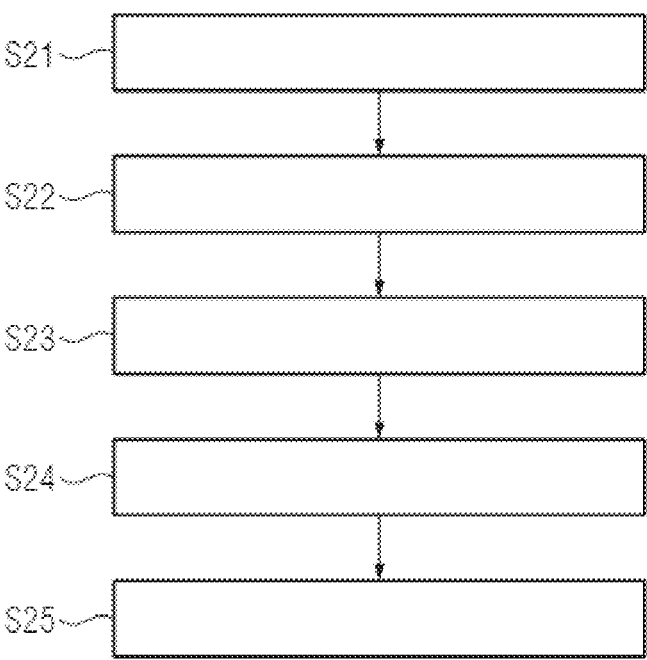
FIG. 3 depicts a flowchart illustrating a method for identifying potential clinical outcomes for a target patient according to an embodiment.

According to some examples, the potential clinical outcomes O1 . . . ON may be determined by finding similar cases with already verified clinical outcomes O1 . . . ON. FIG. 3 shows an exemplary method for finding such similar cases. The order of the steps does not necessarily correspond to the numbering of the steps but may also vary between different embodiments of the present invention.

In a first step S21, a data descriptor is generated from the patient data TPD. The data descriptor may comprise the key features of the patient data TPD in the form of a feature vector. Since the patient data TPD may generally comprise image data as well as non-image data, the data descriptor may likewise be based on image feature signatures and non-image features. Feature signatures may be generated by image analysis methods comprising the identification, analysis and/or measurement of objects, local and or global structures and/or textures present in any image data comprised in the patient data TPD. The generated image feature signature may comprise an anatomical feature and/or structure, like e.g. the presence of a landmark or the size of an organ or a structure, texture and/or density of an identified tissue or organ. The feature signatures may likewise comprise a parameter characterizing a color and/or grey scale scheme or contrast characteristics or local gray scale gradients present in the analyzed image. The image feature signatures preferably comprise not only one but numerous features which as a sum characterize the analyzed image.

The feature signatures extracted from the non-image data comprised in the patient data TPD may comprise metadata associated to the image data. Further, they may relate to data independent form the image data providing further context information with regard to the target patient, such as features extracted from the electronic health record, laboratory data, and the like.

In some examples, the step of generating a data descriptor S21 is carried out using a trained machine-learning algorithm (also denoted as trained function). Preferably, the trained machine-learning algorithm comprises a neural network, most preferably a convolutional neural network. A first group of neural network layers may be applied to extract features from images. In this case, medical images, i.e. the gray scale and/or color values for each individual image element of the image, serve as input values for the neural network. The thus extracted features like, contrast, gradients, texture, density, or the like may be fed as input values to a second group of network layers, also known as classifiers, which serve to further assign objects and/or characteristics to at least one of the extracted features present in the image. Similarly, non-image features may be extracted from non-image data and subsequently classified.

At step S22 of FIG. 3, the data descriptor extracted from the patient data TPD is used to query the similar case database 40. To this end, the data descriptor of the target patient may be compared to corresponding data descriptors of reference patients the patient data RPD of which is stored in the similar case database 40. The data descriptors of the reference patients may be generated in the same way as the data descriptor for the target patient. According to some examples, the data descriptors of the reference patients have been generated before the actual query of step S22 and are stored together with the references patient data sets RPD in similar case database 40.

In subsequent step S23, the method comprises determining a similarity metric representing a similarity between the data descriptor of the target patient and the data descriptors of at least a part of the reference cases in the similar case database 40. In some examples, the similarity metric may be a distance in vector space between the data descriptor of the target patient and the data descriptors of the reference cases. For example, the distance may be the Euclidean distance between the two points in vector space that the target and reference data descriptors represent. In some examples, the similarity metric may be the L1 norm of the reference data descriptor vector and the target data descriptor vector. In some examples, other similarity metrics may be used, such as a cosine similarity between the data descriptors. For each reference case taken into account, the similarity metric may represent how similar the reference case is to the target patient. In other words, the similarity metric expresses (quantifies) a degree of similarity between the target patient and a respective reference patient.

Next, in step S24 of FIG. 3, the degrees of similarity determined in step S23 may be used to select those reference patients (reference patient data sets RPD) having the greatest similarity to the target patient (the patient data TPD of the target patient). According to some examples, all reference cases may be taken into account the degree of similarity to the target patients of which is greater than a predetermined threshold.

Due to the similarity between the target patient and the selected similar cases, there is a certain likelihood that the known clinical outcomes of the similar cases may also be applicable to the target patient at hand. This concept is exploited at step S25 of FIG. 3. In this step, potential clinical outcomes O1 . . . ON for the target patient are compiled from the known clinical outcomes of the selected similar cases. If, for instance, several similar cases have a decision for performing a biopsy on record as a clinical outcome, the very same clinical outcome may also be suggested for the target patient. Likewise, verified diagnosis results of the similar cases may also come into question as potential clinical outcomes O1 . . . ON of the target patient. According to some examples, all known clinical outcomes of the similar cases may be made potential clinical outcomes O1 . . . ON of the target case. Alternatively, the known clinical outcomes may be grouped into categories such as 'therapy', 'prognosis', 'further actions' or 'diagnosis' and only known clinical outcomes falling into one or more distinct categories may be considered as potential clinical outcomes O1 . . . ON for the target patient. According to some examples, these distinct categories may be selectable by the user via user interface 10.

Self-speaking, there are also other ways of compiling the potential clinical outcomes O1 . . . ON for the target patient. For instance, the aforementioned data descriptor of the target patient may be used to query a knowledge database including but not limited to online textbooks or cockpits, such as Thieme's eRef or Radiopedia. In addition or as an alternative, the potential clinical outcomes O1 . . . ON may be taken from clinical workflows or guidelines, suggesting a certain diagnosis or action plan for a certain case.

Once the potential clinical outcomes O1 . . . ON have been determined, their relevance for the target patient is evaluated. To this end, probabilities PO1 . . . PON are calculated at step S30 of FIG. 2. For each potential clinical outcome O1 . . . ON, a probability PO1 . . . PON is calculated. The probabilities PO1 . . . PON may be seen as measures for the likelihood that a certain clinical outcome O1 . . . ON applies for the target patient.

According to some examples, the probabilities PO1 . . . PON may be calculated based on the degrees of similarities optionally calculated in steps S21 to S25. The underlying reasoning is that, if a comparable high degree of similarity could be ascertained between the patient data TPD of the target patient and the patient data RPD of a reference case, there naturally is a rather high likelihood that the clinical outcomes of the reference case are as well applicable to the target patient.

In addition or as an alternative, probabilities PO1 . . . PON may be accorded to the potential clinical outcomes O1 . . . ON by comparing the patient data TPD to distribution data representing the occurrences of certain clinical outcomes in a population of patients. The reasoning is that certain parameters of the target patient may indicate that certain clinical outcomes are more likely than others. For example, such parameters may be the patient's age, gender, or weight. If, for instance, the target patient is male, the likelihood of having a certain disease may be very different compared to female patients. As yet another example, the probability that a given diagnosis or treatment recommendation applies may considerably depend on the body mass index of the target patient. Such statistical effects may be quantified by distribution data showing the occurrence probability of a clinical outcome versus a parameter drawn from the patient data (such as age, weight, sex, etc.). In some examples, the distribution data may be binomial, such as for smoking status (i.e. smoker and non-smoker). In some examples, the distribution data may be continuous or quasi continuous, such as for age. In some examples, the distribution data may be derived from a cohort of reference patient data sets RPD, e.g., as stored in the similar case database 40. For each of a plurality of clinical outcomes, reference patient data where the clinical outcome has been recorded may be extracted, and the distribution of the clinical outcome may be determined. In some examples, the distribution data may be determined from empirical studies, for example as published in medical journals or textbooks. In some examples, the distribution data may be determined by consolidating empirical distribution information from a plurality of sources, for example from medical articles.

Noteworthy, the comparison to the distribution data may also be used to modify and/or filter the determined potential clinical outcomes O1 . . . ON as, for instance, derived using a similar patient search according to steps S21 to S25. If, for instance, a high degree of similarity suggests that a certain clinical outcome could also be indicated by the patient data TPD of the target patient, but a criterion for exclusion applies for this clinical outcome (for instance, if the clinical outcome is gender-specific), this may be compensated for by a comparison to appropriate distribution data for the clinical outcome in question.

Figure 4:
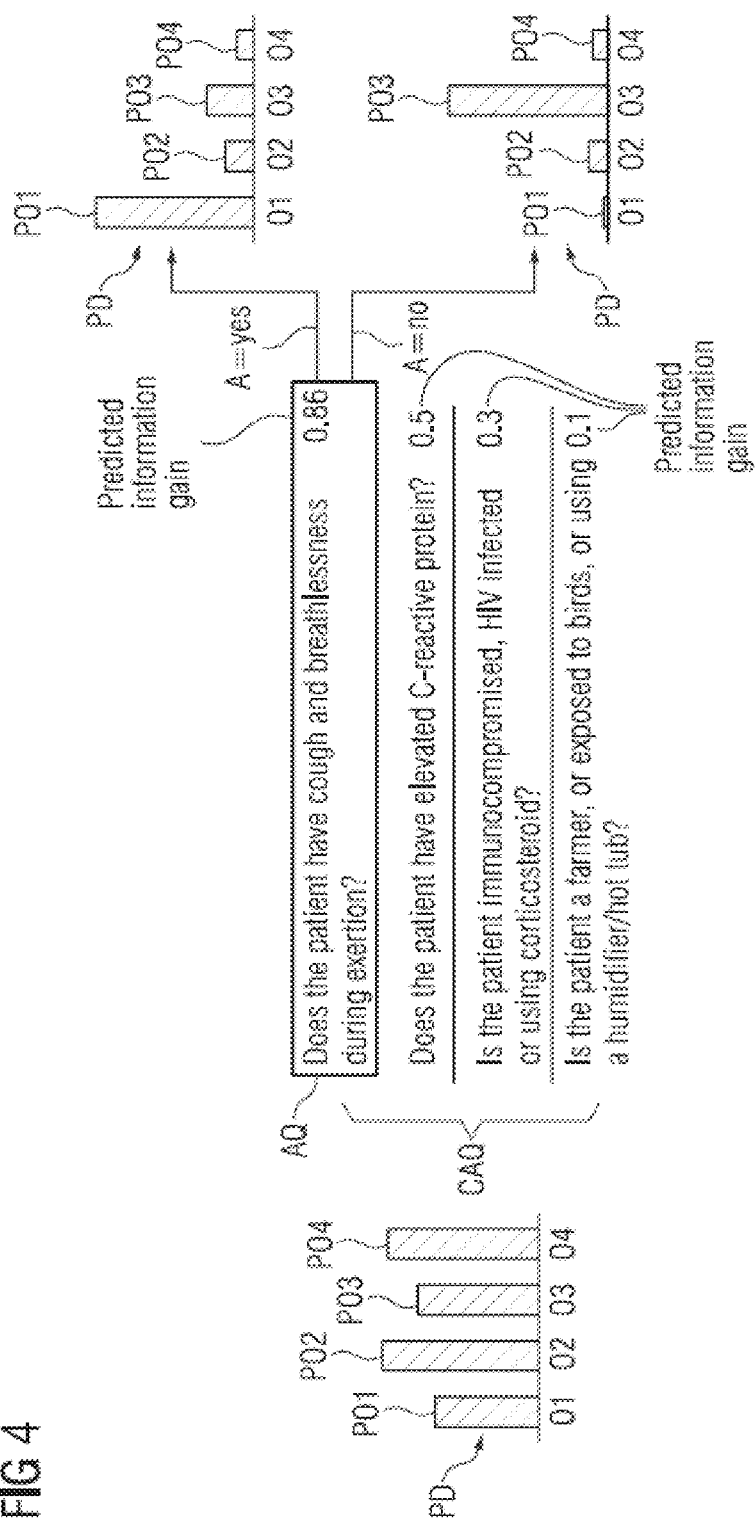
FIG. 4 schematically shows the adaptation of the probabilities according to an embodiment.

In any case, step S30 results in a number of automatically derived clinical outcomes O1 . . . ON which are more or less relevant for the target patient. The relevance is measured by the corresponding probabilities PO1 . . . PON. In other words, a probability distribution PD results for the potential clinical outcomes O1 . . . ON, as shown in FIG. 4.

Especially if many potential clinical outcomes O1 . . . ON come into question or if several—possibly conflicting—clinical outcomes O1 . . . ON have comparable probabilities, it may be very difficult for the user to pick the most relevant clinical outcomes O1 . . . ON from the selection of clinical outcomes O1 . . . ON provided. To alleviate this problem, the method foresees narrowing the selection of potential clinical outcomes O1 . . . ON and/or making the selection of clinical outcomes O1 . . . ON more unambiguous in terms of the probabilities PO1 . . . PON (i.e., the probability distribution PD). To do so, it is envisioned to "ask" the user one or more anamnestic questions AQ that would be helpful for narrowing down the selection and/or sharpening the probability distribution PD of the clinical outcomes O1 . . . ON.

The selection of these anamnestic questions AQ happens at step S40. To this end, step S40 foresees accessing database 30 storing a set of pre-configured candidate anamnestic questions CAQ and selecting one or more anamnestic questions AQ that are relevant for the target patient (also see FIG. 4). According to some examples, the system may be configured to select the 'best' anamnestic question(s) AQ for the case at hand. The 'best' anamnestic questions according to such a scenario AQ those which reduce the uncertainty the most. According to some examples, the best anamnestic question(s) AQ may be determines based on the probability distribution PD determined at step S30. Specifically, the probability distribution PD may be analyzed for the predicted impact the answers to the candidate anamnestic questions CAQ would have. In other words, such analysis may be perceived as the determination of which additional knowledge not yet reflected in the patient data TPD (and therefore not used during the search for relevant clinical outcomes O1 . . . ON) would be helpful for ruling out or verifying a potential clinical outcome O1 . . . ON.

Step S40 may rely on aforementioned distribution data for one or more of the clinical outcomes O1 . . . ON in a population of patients measuring the occurrence or indication of a clinical outcome O1 . . . ON as a function of the patients' characteristics or variables. If, for instance, the analysis up to step S30 prompted high probabilities PO1 . . . PON for Lymphocytic Interstitial Pneumonia and Idiopathic Pulmonary Fibrosis, a comparison of the respective gender distributions of these diseases could help to further clarify the diagnosis. While the prevalence of Lymphocytic Interstitial Pneumonia in females is three times that in males, Idiopathic Pulmonary Fibrosis has a slightly higher prevalence in males. Accordingly, system 1 would automatically select the anamnestic question AQ for the gender of the patient (if not already known from the patient data TPD) from the pre-configured candidate anamnestic questions CAQ.

Mathematically, the principle of finding anamnestic questions AQ which reduce the uncertainty the most can be quantified by calculating the entropy reduction (i.e., the information gain) a hypothetical answer to a anamnestic question AQ would bring about for the probability distribution PD. Since the answer is not known a priori, an upper bound for the entropy reduction may be calculated in step S40. Specifically, it is proposed to calculate the weighted maximum possible entropy reduction as a metric for selecting appropriate anamnestic questions, which may be expressed as:

$$\mathrm{MAX}(P(\mathrm{yes})[H(PD|TPD)-H(PD|TPD,A=\mathrm{yes})],P(\mathrm{no})$$
$$[H(PD|TPD)-H(PD|TPD,A=\mathrm{no})]).$$

Thereby, H(PD|TPD) is the initial entropy of the probability distribution PD of the calculated probabilities PO1 . . . PON of the patient data TPD, H(PD|TPD, Q=yes) is the entropy of the probability distribution PD assuming a yes as answer A to question AQ, H(PD|TPD, Q=no) being the entropy of the probability distribution PD assuming a no as answer to question AQ, P(yes) is the probability for answering AQ with 'yes', and P(no) is the probability for answering AQ with 'no'. The entropies of 'yes' and 'no' responses are weighted by their likelihood to obtain weighted information gain after the response. The difference between prior entropy and joint entropy is the information gain as given in the formula.

According to some examples, the system may also be configured to select a fixed set of questions according to one or more relevant medical guidelines applicable to the target patient and/or according to the aforementioned categories of the clinical outcome O1 . . . ON.

Once one or more appropriate anamnestic question AQ have been selected in step S40, they are presented to the user at step S50. According to some examples, anamnestic questions AQ may be asked using a continuous conversational interface. The presentation of the anamnestic questions AQ may either be a visual presentation by displaying the anamnestic questions AQ in a graphical user interface GUI running in the user interface 10. In addition to that or as an alternative, the anamnestic questions AQ may be read to the user. To this end, the question texts may be converted to speech using existing speech APIs or by training a new text2speech model. Additionally, visualizing a popup could help a user to reread if this is needed. According to some examples only the best anamnestic question AQ (the one that reduces the uncertainty the most) is shown to the user. According to other examples, a list comprising more than one anamnestic question AQ is presented to the user.

At subsequent step S60, the answers A of the user are collected via user interface 10. Answers A may be provided by inputting text into user interface 10, clicking buttons in a graphical user interface GUI running in user interface 10, by speech which is converted to text by an appropriate language processing module, or any other suitable way of inputting data in system 1. In principle, the user may answer by inputting 'yes' or 'no'. Further, he may input more specific data (such as the age). In addition, the user may be given the possibility to answer with 'unknown' when he has no access to the requested information.

At subsequent step S70, the impact of the user's answers to the probabilities PO1 . . . PON is evaluated. In other words, the probabilities PO1 . . . PON and therewith the probability distribution PD are adapted (c.f., FIG. 4).

That followed, in optional step S80, the result of the computation and, in particular, the clinical outcomes O1 . . . ON may be displayed to the user. Preferably, the output is such that the confidence of the respective clinical outcome O1 . . . ON is perceivable for the user. Further, the presentation of the clinical outcomes O1 . . . ON to the user may be enriched with auxiliary information, which auxiliary information may, for instance, pertain to similar cases or information extracted from one or more knowledge databases. Further details regarding the machine-user-interaction will be given in the following in conjunction with FIGS. 5 to 9.

Step S90 is a repeat step indicating that steps S40 to S80, i.e., the selection of one or more anamnestic questions AQ (S40), the presentation of the selected anamnestic questions AQ to the user (S50), the receipt of the corresponding answers A of the user (S60), the adaptation of the probabilities PO1 . . . PON (S70), and the optional display of the results (S80), may be repeated multiple times. In each pass, the anamnestic questions AQ may be selected based on the adjusted probabilities PO1 . . . PON of the preceding iteration. This may have the effect that the entropy of the probability distribution PD of the clinical outcomes O1 . . . ON is reduced more and more and the procedure converges to the most probable clinical outcomes O1 . . . ON. Steps S40 to S80 may be repeated until an acceptable confidence level has been reached. This may be achieved once the relative probability PO1 . . . PON of at least one of the potential clinical outcome O1 . . . ON is higher than a predetermined threshold.

Figure 5:
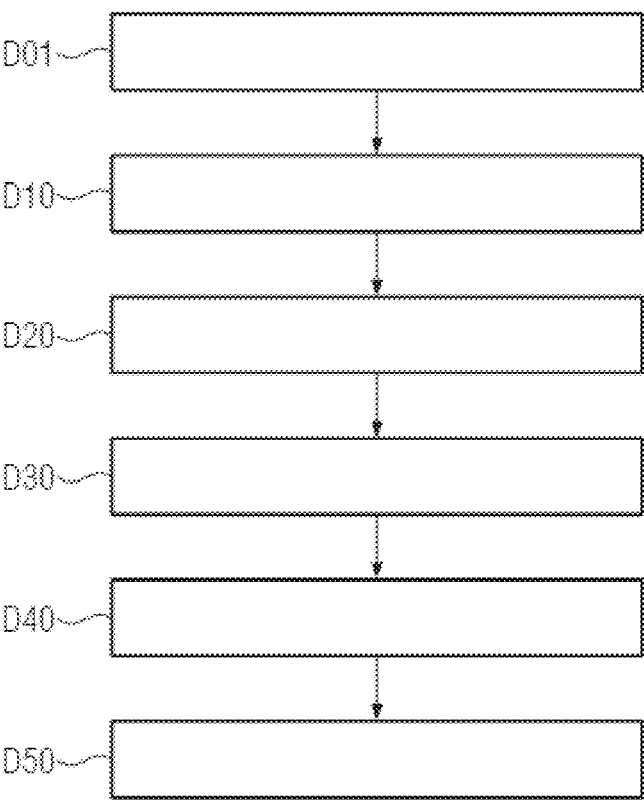
FIG. 5 depicts a flowchart illustrating a workflow facilitating human-machine interactions in a clinical decision support system according to an embodiment.

FIG. 5 depicts optional method steps for facilitating a continuous human machine interaction according to an embodiment. The order of the steps does not necessarily correspond to the numbering of the steps but may also vary between different embodiments of the present invention. A representation of a corresponding graphical user interfaces GUIs are shown in FIGS. 6 to 9.

At step D01 shown in FIG. 5, the user may select the target patient to be reviewed, e.g., from a worklist or a patient browser.

At subsequent step D10, the relevant information of the target patient may be displayed. This information may be derived from the patient data TPD of the selected target patient. As shown in FIGS. 6 to 9, the displayed relevant information may include image data 110 (which may be presented in the form of a thumbnail) and non-image data 120 (which may be presented as textual information or in the form of one or more graphs). According to some examples, the information pertaining to the target patient is displayed in a first display area 100 of the graphical user interface GUI.

Further, the graphical user interface GUI may include a second display area 200 different than the first area 100, where potential clinical outcomes O1 . . . ON for the target patient may be shown at step D20. As explained in connection with FIG. 3, the potential clinical outcomes O1 . . . ON may be retrieved by way of a similar case search for finding reference patient data sets RPD having a certain degree of similarity to the patient data TPD of the target patient. Each of the similar cases may indicate a known clinical outcome which may be relevant for the target patient. In general, all or only part of the determined potential clinical outcomes O1 . . . ON may be displayed. If only part of the potential clinical outcomes O1 . . . ON are displayed in the second display area 200, the presentation may be such that only the most relevant clinical outcomes O1 . . . ON (i.e., those with the highest probabilities PO1 . . . PON) are shown, at least initially. Optionally, the graphical user interface GUI may include a button 201 for displaying further clinical outcomes O1 . . . ON.

In the example shown in FIGS. 5 to 9, the potential clinical outcomes O1 . . . ON relate to a diagnosis. According to the example of FIGS. 5 to 9, the diagnoses that come into question for the target patient as potential clinical outcomes O1 . . . ON are shown as disease names in the graphical user interface GUI. However, this is to be construed by way of example and not as limitation as the graphical user interface GUI may also indicate other clinical outcomes O1 . . . ON such as predicted therapy responses, further actions, or the prognosis and so forth. The retrieval of potential clinical outcomes O1 . . . ON (e.g., by way of a similar case search) may be initiated automatically once the case of the target patient has been opened. As an alternative, the retrieval of potential clinical outcomes O1 . . . ON may be initiated by the user, e.g., by clicking on an appropriate action button 310 in the graphical user interface GUI. Further, as yet a further option, the graphical user interface may include buttons 312 for selecting the category of the potential clinical outcomes O1 . . . ON to be retrieved.

Each of the displayed potential clinical outcomes O1 . . . ON may be provided a designated display area or box 230, 231, 230', 231', 232' which provides space for displaying auxiliary information associated to the respective clinical outcome O1 . . . ON.

As mentioned, the potential clinical outcomes O1 . . . ON may be ranked according to the underlying probabilities PO1 . . . PON that they are indicated by the patient data TPD of the target patient. To make this ranking accessible the arrangement of the information displayed in the graphical user interface GUI may be configured such that the ranking becomes perceivable for a user. In the example provided in FIGS. 5 to 8, this is realized by an vertically ordered list of potential clinical outcomes O1 . . . ON. The higher the probability PO1 . . . PON of the potential clinical outcome O1 . . . ON, the farther up the corresponding box 230 and 231 is shown in the second display area 200 of the graphical user interface GUI. In the example shown in FIGS. 5 and 6, 'Disease Name A' would thus have a higher probability P01 of being indicated by the target patient than 'Disease Name B'.

Figure 8:
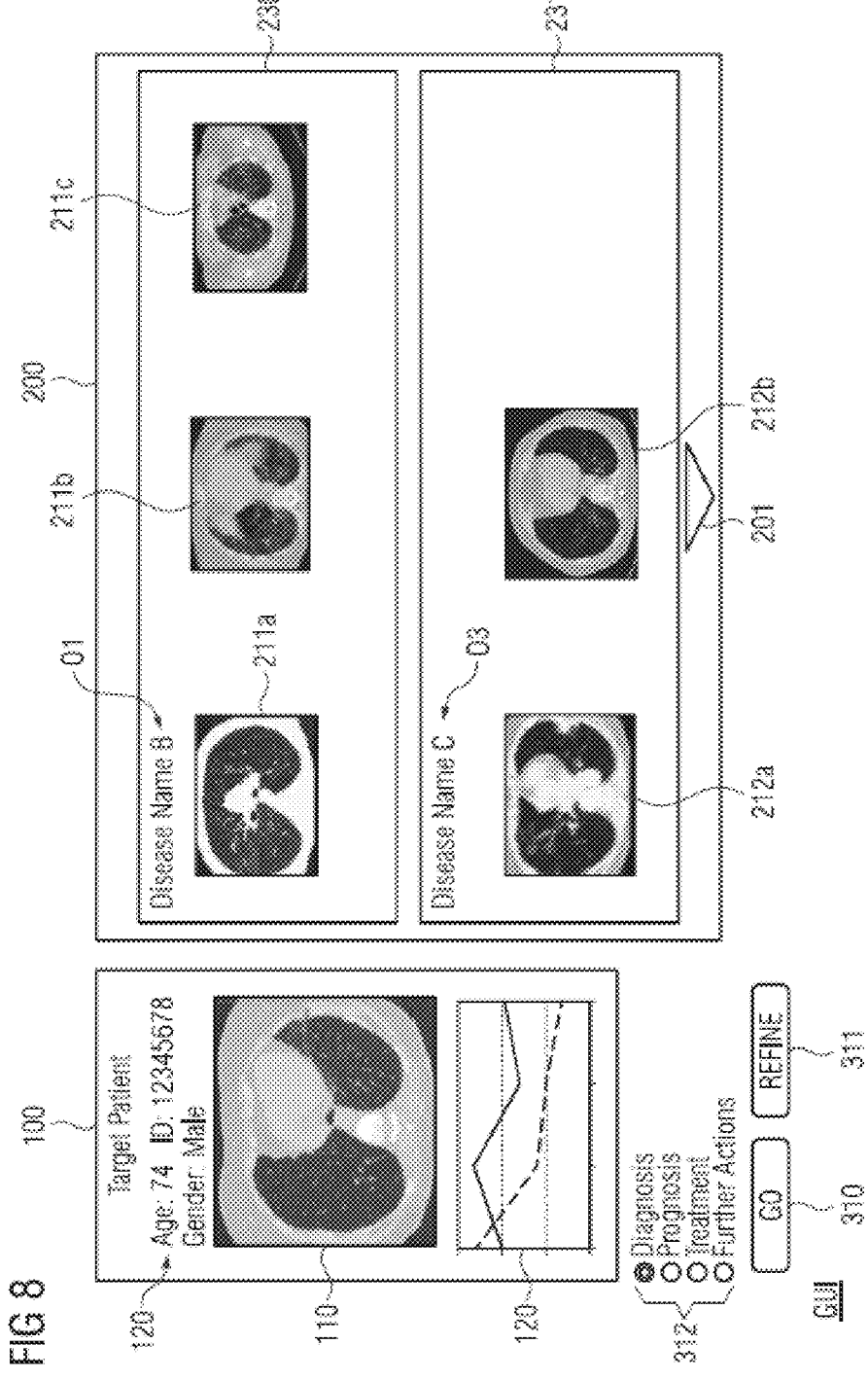
Figure 9:
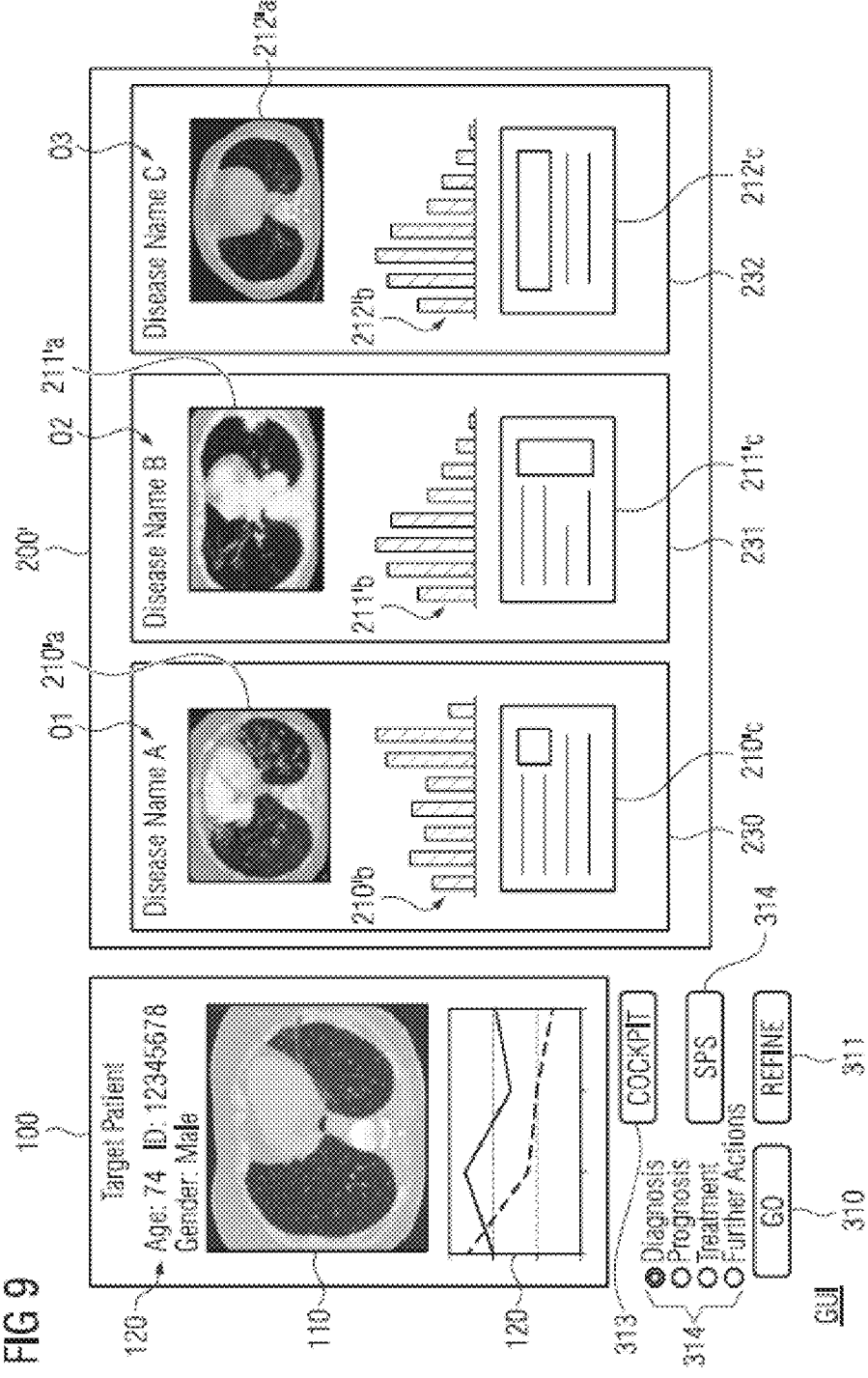

According to another sample graphical user interface GUI shown in FIG. 9, the potential clinical outcomes O1 . . . ON may also be arranged horizontally in second display area 200'. Like in the examples shown in FIGS. 6 to 8, each of the displayed potential clinical outcomes O1 . . . ON is shown in a dedicated box 230', 231', 232'. To further highlight the ranking for the user, the potential clinical outcomes O1 . . . ON may be additionally provided with numbers in display fields 240', 241', 242' indicating their current rank among the potential clinical outcome O1 . . . ON. According to some examples, instead of ranking numbers, display fields 240', 241', 242' may also indicate the probabilities PO1 . . . PON (or some derived confidence score).

Figure 6:
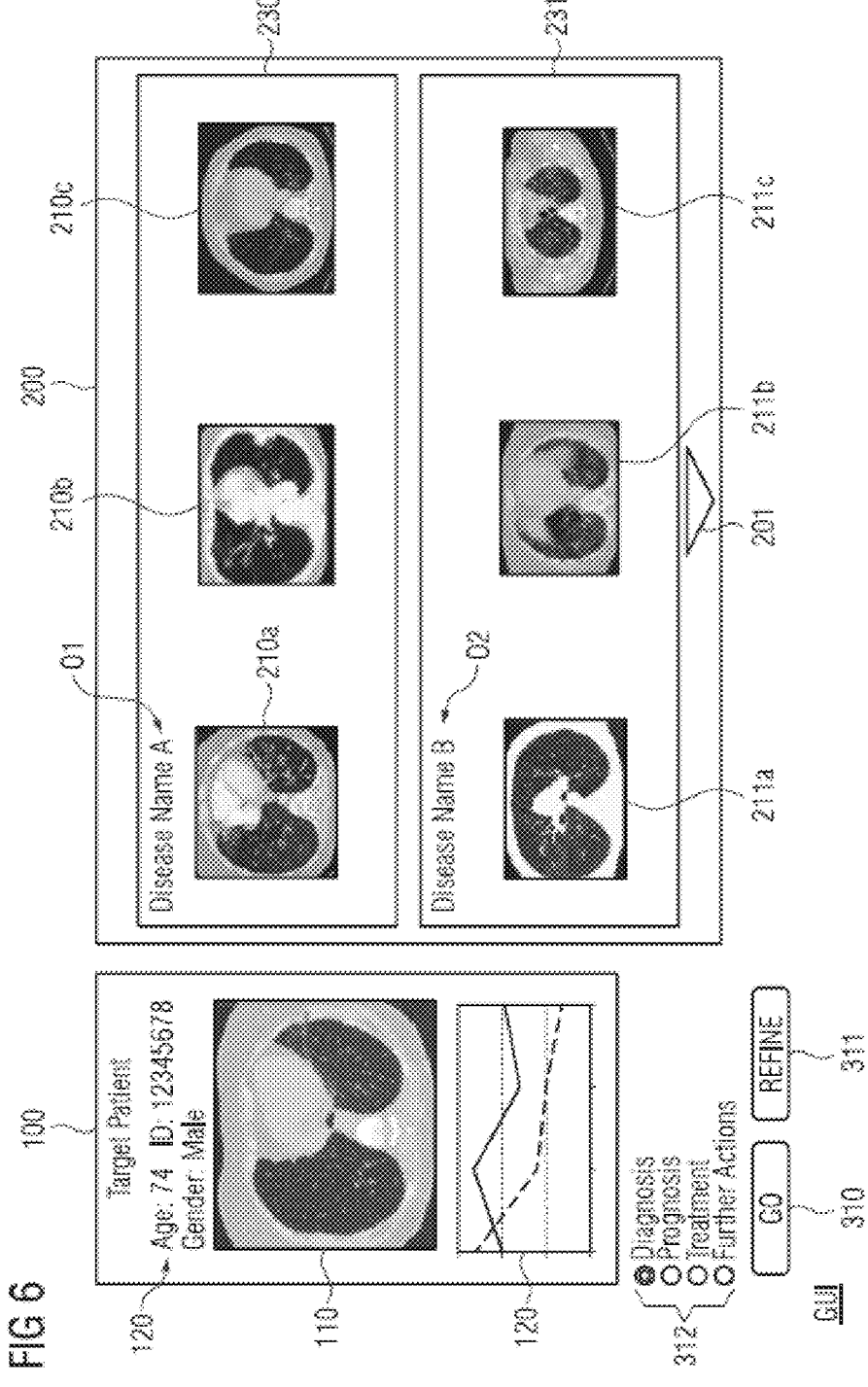
FIGS. 6 to 9 schematically show graphical user interfaces for facilitating user-machine interactions in a clinical decision support system according to embodiments.
Figure 7:
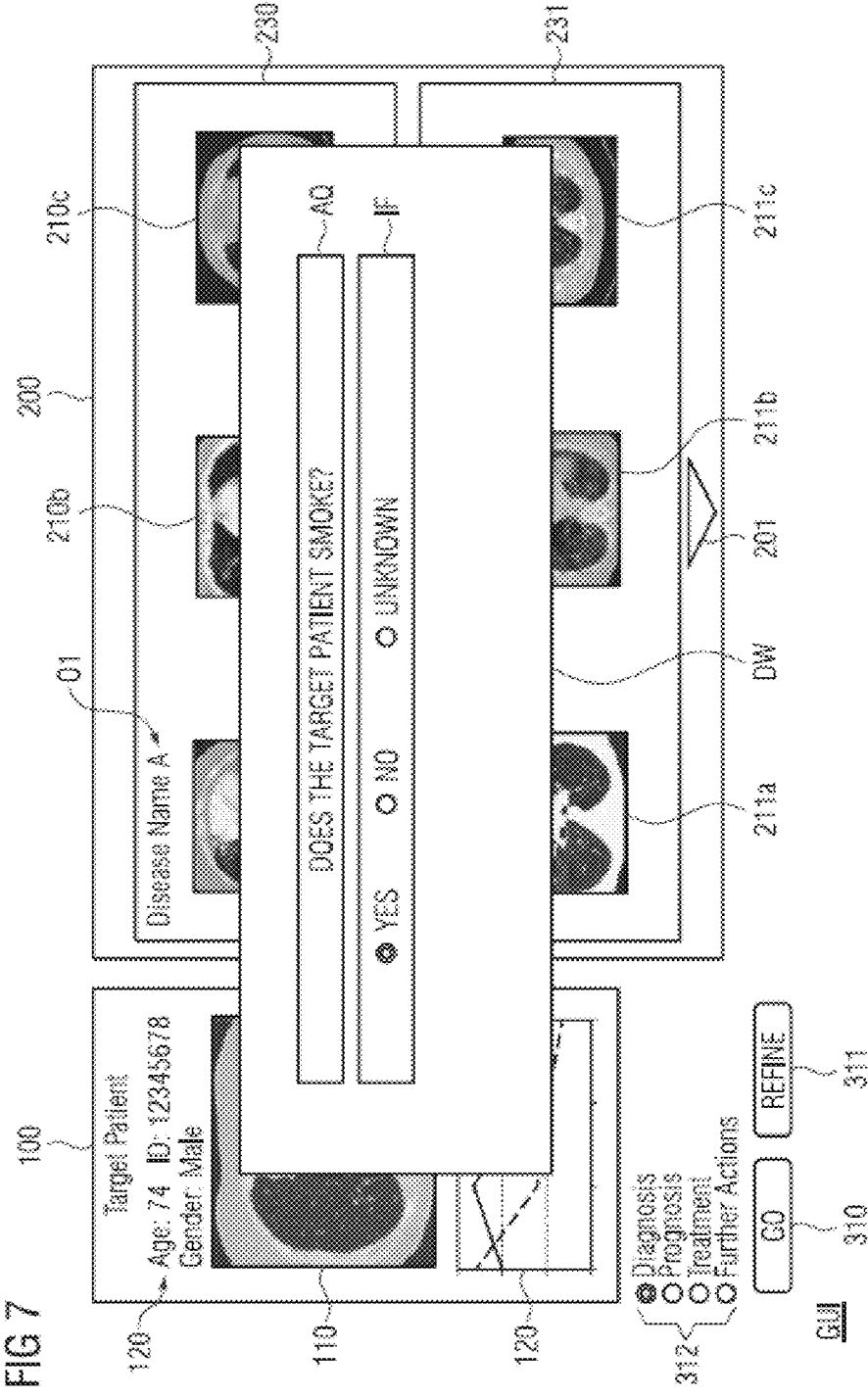

To provide further assistance to the user, the presentation of the potential clinical outcomes O1 . . . ON may be enriched with auxiliary information pertaining to the respective clinical outcome O1 . . . ON. This auxiliary information may be displayed as data items 210a-210c, 211a-211c, 210'a-210'c, 211'a-211'c, 212'a-212'c. As shown in FIGS. 6 to 8, the data items 210a-210c, 211a-211c may include image data which is displayed in the form of thumbnails. In particular, this image data may pertain to patients similar to the target patient and the thumbnails may show images which are morphological similar to image data 110 available for the target patient. This is to be construed by way of example and as limitation, as the presentation of the similar patient data may include different or additional information. This is exemplified by FIG. 9, where some data items 210'b, 211'b, 212'b further include distribution data and other data items 210'c, 211'c, 212'c information extracted from online textbooks or cockpits. Data items 210'a, 211'a, 212'a may relate to data taken from similar patients (such as similar images) or to reference data (specifically: reference images) excerpted from a compendium such as an online textbook like Thieme's eRef.

As shown in FIGS. 6 to 9, the auxiliary data items 210a-210c, 211a-211c, 210'a-210'c, 211'a-211'c, 212'a-212'c are arranged in the respective display areas or boxes 230, 231, 232, 230', 231' of the their corresponding clinical outcomes O1 . . . ON. With that they are visually grouped according to their corresponding clinical outcomes O1 . . .

ON and, thereby, implicitly arranged according to the ranking established for the clinical outcomes O1 . . . ON.

According to some examples, the graphical user interface GUI may comprise buttons 313, 314 for switching between the presentation of FIGS. 6 to 8 which is more or less focused on the similar patient search ('SPS') or the presentation of FIG. 9 which provides a more holistic picture ('cockpit').

Once potential clinical outcomes O1 . . . ON and corresponding probabilities PO1 . . . PON have been calculated (and displayed), the inventive system and method envision to present one or more anamnestic questions AQ to user which might help to further clarify the clinical picture of the target patient. The routine for retrieving and presenting these anamnestic questions AQ may be initiated automatically by the system and method or started upon user request, e.g., by clicking on an optional action button 320 provided in the graphical user interface GUI.

The one or more anamnestic questions AQ thus retrieved are then presented to the user at step D30 and answers A are collected at step D40. According to an exemplary embodiment shown in FIG. 7, one or more anamnestic questions AQ may be presented by way of a dialogue window DW which may be overlaid over the first and/or second display areas 100, 200. Dialogue window may comprise the anamnestic questions AQ and input fields IF for the user in order to answer the questions. The input fields IF may comprise free text fields or radio buttons. As an alternative, the one or more anamnestic questions AQ may also be presented in a separate display area of the graphical user interface GUI (instead of in the form of an overlaid dialogue window DW). In addition to that or as an alternative, the questions may be read to the user and the spoken answer A of the user may be recorded and evaluated using a speech recognition module.

Once the answers A of the user where received in step D40, the method calculates the impact of the answers A on the probabilities PO1 . . . PON of the potential clinical outcomes O1 . . . ON as described in connection with FIGS. 2 to 5. This may lead to a change in the relevance of the potential clinical outcomes O1 . . . ON for the target patient. In step D50, the graphical user interface is adapted accordingly. Clinical outcomes O1 . . . ON that now rank higher are moved up ('Disease Name B' and the corresponding thumbnails are shown at the top of the results area 200 in FIG. 8). Further, clinical outcomes O1 . . . ON which are not that probable any more may even be removed ('Disease Name A' and the corresponding thumbnails 210a-210c have been removed from the presentation in FIG. 7). In lieu thereof, other clinical outcomes O1 . . . ON may be added to the presentation ('Disease Name C' and thumbnails 212a, 212b). The adaptation of the presentation in step D50 may take place after every iteration of steps S40 to S70. As an alternative, the presentation is only updated once a sufficient certainty level as to the potential clinical outcomes O1 . . . ON has been reached after several iterations of anamnestic questions AQ and answers A. The latter has the advantage that there may be less confusion on the side of the user as the presentation is steadier. In addition, the computational costs for updating the graphical user interface GUI may be reduced.

Once the graphical user interface GUI as been updated according to the adapted probabilities PO1 . . . PON, the user may either accept the results and base his clinical decision on the potential clinical outcomes O1 . . . ON hitherto derived, or she or he may request an additional set of anamnestic questions AQ if he feels that the uncertainty needs to be reduced even further. In that case, he may again activate the process by clicking on optional action button 311.

Wherever meaningful, individual embodiments or their individual aspects and features can be combined or exchanged with one another without limiting or widening the scope of the present invention. Advantages which are described with respect to one embodiment of the present invention are, wherever applicable, also advantageous to other embodiments of the present invention.

The following points are also part of the disclosure:

1. Computer-implemented method for clinical decision support, the method comprising the steps of:

receiving patient data of a target patient;

determining, based on the patient data, a number of potential clinical outcomes associated with the target patient;

calculating, for each of the potential medical outcomes, a probability of being indicated by the patient data;

based on the probabilities, selecting one or more anamnestic questions from a set of pre-configured anamnestic questions stored in a database;

presenting the one or more selected anamnestic questions to a user via a user interface;

receiving one or more answers to the one or more selected anamnestic questions from the user via the user interface;

adapting the probabilities based upon the answers.

2. Method according to 1, wherein the step of determining comprises:

identifying, from a set of reference patients different than the target patient and based on the patient data, a number of similar patients, wherein each similar patient has a degree of similarity to the target patient and is associated to at least one known clinical outcome;

compiling the potential clinical outcome from the known clinical outcomes of the identified similar patients.

3. Method according to 2, wherein the step of identifying a number of similar patients comprises:

calculating a data descriptor from the patient data of the target patient, receiving, for each reference patient of the set of reference patients, a corresponding data descriptor;

determining, for each reference patient a similarity metric representing the degree of similarity between the data descriptor of the target patient and the data descriptor of the reference patient; and selecting one or more reference patients as similar patients based on the respective similarity metrics.

4. Method according to 2 or 3, further with the step of retrieving, for all or part of the similar patients, data items form patient data of the similar patients;

displaying part or all of the data items in conjunction with all or part of the clinical outcomes to the user via the user interface in a presentation configured such that the association of the data items to the corresponding potential clinical outcome becomes perceivable for the user;

wherein the data items preferably comprise medical image data pertaining to the respective similar patient.

5. Method according to 4, further with the steps of:

establishing a ranking of the potential clinical outcomes according to their respective probabilities, and displaying the potential clinical outcomes to the user via the user interface in the presentation additionally configured such that the ranking becomes perceivable for the user.

6. Method according to any of the preceding points, wherein the step of selecting one or more anamnestic questions and/or the step of calculating, for each of the potential medical outcomes, a probability of being indicated by the patient data and/or the step of adapting the probabilities is/are based on distribution data representing a distribution of one or more of the potential clinical outcomes as a function of one or more sample parameters of a population of patients.

7. Method according to 6, wherein one or more of the selected anamnestic questions address at least one of the sample parameters.

8. Method according to any of the preceding points, wherein the patient data includes:

image data depicting a body part of the target patient, and/or image data depicting a sample taken from the target patient, and/or non-image data of the target patient.

9. Method according to any of the preceding claims wherein the medical outcomes include statements relevant for diagnosis and/or therapy decisions and/or prognosis and/or further actions with regard to the target patient.

10. Method according to any of the preceding points, wherein the potential clinical outcomes are diseases and/or injuries potentially linked to the target patient.

11. Method according to any of the preceding points wherein each potential clinical outcome is associated with at least one of a plurality of predetermined categories;

each anamnestic question in the set of anamnestic questions is associated to at least one of the categories; and in the step of selecting only such questions are considered for being selected the at least one associated category of which matches at least one of the categories of the potential clinical outcomes.

12. Method according to 11, wherein the category is selectable by the user from the plurality of predetermined categories via the user interface and only such clinical outcomes are considered in the step of determining the number of potential clinical outcomes the associated category of which matches the selection of the user.

13. Method according to 11 or 12, wherein the plurality of predetermined categories comprises at least one of diagnosis, therapy, prognosis and further actions as categories.

14. Method according to any of the preceding points, wherein the set of pre-configured anamnestic questions have been derived empirically.

15. Computer-implemented method of providing probabilities for potential clinical outcomes for a patient, the method comprising the steps of:

receiving patient data of a target patient;

determining, based on the patient data, a number of potential clinical outcomes associated with the target patient;

calculating, for each of the potential medical outcomes, a probability of being indicated by the patient data;

based on the probabilities, selecting one or more anamnestic questions from a set of pre-configured anamnestic questions stored in a database;

presenting the one or more selected anamnestic questions to a user via a user interface;

receiving one or more answers to the one or more selected anamnestic questions from the user via the user interface;

adapting the probabilities based upon the answers; providing the adapted probabilities.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for clinical decision support, the computer-implemented method comprising:

determining a number of potential clinical outcomes based on patient data, the patient data being of a target patient, the number of potential clinical outcomes being associated with the target patient, the patient data including a plurality of pieces of information, and the determining including generating a target feature vector based on an image feature signature, the image feature signature being generated based on at least one of gray scale values or color values for each image element of image data included in the patient data, determining a plurality of similar patients from among a set of reference patients based on similarities between the target feature vector and corresponding feature vectors of reference patients among the set of reference patients, and determining the number of potential clinical outcomes based on clinical outcomes of the plurality of similar patients;

calculating a respective probability for each corresponding potential clinical outcome among the number of potential clinical outcomes based on similarities between the target feature vector and corresponding feature vectors of the plurality of similar patients to obtain a plurality of probabilities, each respective probability being of the corresponding potential clinical outcome being indicated by the patient data;

calculating an entropy reduction amount corresponding to each respective anamnestic question among a set of anamnestic questions stored in a database, the entropy reduction amount corresponding to the respective anamnestic question being an amount by which an answer to the respective anamnestic question would reduce an entropy of a probability distribution, and the probability distribution including the plurality of probabilities;

selecting a first anamnestic question corresponding to a highest entropy reduction amount from among the set of anamnestic questions;

presenting the first anamnestic question to a user via a user interface;

receiving a first answer to the first anamnestic question from the user via the user interface; and adapting the plurality of probabilities based on the first answer to obtain an adapted plurality of probabilities.

2. The computer-implemented method of claim 1, wherein the set of reference patients is different from the target patient;

each respective similar patient among the plurality of similar patients has a degree of similarity to the target patient and is associated with at least one known clinical outcome; and the determining the number of potential clinical outcomes includes determining the number of potential clinical outcomes from known clinical outcomes of the plurality of similar patients.

3. The computer-implemented method of claim 2, wherein the calculating the respective probability includes calculating the plurality of probabilities based on the degree of similarity of each respective similar patient among the plurality of similar patients.

4. The computer-implemented method of claim 2, further comprising:

mining at least one of the patient data or additional data sources associated with the target patient to obtain at least one corresponding answer to the first anamnestic question before the presenting.

5. The computer-implemented method of claim 1, further comprising:

mining at least one of the patient data or additional data sources associated with the target patient to obtain at least one corresponding answer to the first anamnestic question before the presenting.

6. The computer-implemented method of claim 1, further comprising:

storing information included in the first answer in the patient data.

7. The computer-implemented method of claim 1, further comprising:

establishing a ranking of the number of potential clinical outcomes according to the plurality of probabilities; and displaying the number of potential clinical outcomes to the user via the user interface according to the ranking.

8. The computer-implemented method of claim 7, further comprising:

retrieving auxiliary information associated with one or more corresponding potential clinical outcomes among the number of potential clinical outcomes; and displaying the auxiliary information in conjunction with the one or more corresponding potential clinical outcomes.

9. The computer-implemented method of claim 7, further comprising:

repeating the selecting, the presenting, the receiving, and the adapting based on the adapted plurality of probabilities until the respective probability for at least one among the number of potential clinical outcomes exceeds a threshold.

10. The computer-implemented method of claim 9, further comprising:

repeating the establishing and the displaying the number of potential clinical outcomes based on the adapted plurality of probabilities.

11. A non-transitory computer program product storing program elements which induce at least one processor of a system for clinical decision support to perform the computer-implemented method of claim 1 when the program elements are loaded into a memory of the system and executed by the at least one processor.

12. A non-transitory computer-readable medium storing program elements, readable and executable by at least one processor of a system for clinical decision support, that cause the system to perform the computer-implemented method of claim 1 when the program elements are executed by the at least one processor.

13. The computer-implemented method of claim 1, wherein the presenting presents the first anamnestic question and one or more input fields on the user interface; and the receiving includes receiving the first answer via the one or more input fields on the user interface.

14. The computer-implemented method of claim 13, further comprising:

displaying the user interface including a first display area and a second display area, the first display area including at least a portion of the patient data, and the second display area including at least a portion of the number of potential clinical outcomes in first positions according to the respective probability for each corresponding potential clinical outcome; and displaying an updated second display area in response to the adapting, the updated second display area including one or more among the at least the portion of the number of potential clinical outcomes in second positions according to the adapted plurality of probabilities, the second positions being different from the first positions.

15. The computer-implemented method of claim 14, wherein the one or more among the at least the portion of the number of potential clinical outcomes includes fewer potential clinical outcomes than the at least the portion of the number of potential clinical outcomes.

16. The computer-implemented method of claim 15, wherein the user interface includes an action button; and the presenting is performed in response to a first selection of the action button.

17. The computer-implemented method of claim 16, further comprising:

repeating the presenting, the receiving and the adapting based on the displaying the updated second display area in response to a second selection of the action button.

18. The computer-implemented method of claim 1, wherein the patient data includes medical image data; and the computer-implemented method further comprises:

generating the medical image data using a medical imaging modality, the medical imaging modality being configured to generate the medical image data using X-rays, magnetic resonance, positron-emission or ultrasound, and the medical image data including pixels or voxels representative of intensity or absorption; and displaying the medical image data on the user interface.

19. The computer-implemented method of claim 1, wherein the calculating the entropy reduction amount includes calculating the entropy reduction amount corresponding to each respective anamnestic question including applying a respective weight corresponding to an entropy change for each potential answer to the respective anamnestic question.

20. The computer-implemented method of claim 1, wherein the answer to the respective anamnestic question is either 'yes' or 'no'.

21. The computer-implemented method of claim 1, wherein each respective anamnestic question among the set of anamnestic questions asks for personal information of the target patient, a risk factor of the target patient or a medical history of the target patient.

22. A system for clinical decision support, the system comprising:

an interface;

a database storing a set of anamnestic questions; and a computing unit configured to determine a number of potential clinical outcomes based on patient data, the patient data being of a target patient, the number of potential clinical outcomes being associated with the target patient, the patient data including a plurality of pieces of information, and the determination including generating a target feature vector based on an image feature signature, the image feature signature being generated based on at least one of gray scale values or color values for each image element of image data included in the patient data, determining a plurality of similar patients from among a set of reference patients based on similarities between the target feature vector and corresponding feature vectors of reference patients among the set of reference patients, and determining the number of potential clinical outcomes based on clinical outcomes of the plurality of similar patients, calculate a respective probability for each corresponding potential clinical outcome among the number of potential clinical outcomes based on similarities between the target feature vector and corresponding feature vectors of the plurality of similar patients to obtain a plurality of probabilities, each respective probability being of the corresponding potential clinical outcome being indicated by the patient data, calculate an entropy reduction amount corresponding to each respective anamnestic question among the set of anamnestic questions, the entropy reduction amount corresponding to the respective anamnestic question being an amount by which an answer to the respective anamnestic question would reduce an entropy of a probability distribution, and the probability distribution including the plurality of probabilities, select a first anamnestic question corresponding to a highest entropy reduction amount from among the set of anamnestic questions, present the first anamnestic question to a user via the interface, receive a first answer to the first anamnestic question from the user via the interface, and adapt the plurality of probabilities based on the first answer.

23. A system for clinical decision support, the system comprising:

an interface;

a database storing a set of anamnestic questions; and at least one processor configured to determine a number of potential clinical outcomes based on patient data, the patient data being of a target patient, the number of potential clinical outcomes being associated with the target patient, the patient data including a plurality of pieces of information, and the determination including generating a target feature vector based on an image feature signature, the image feature signature being generated based on at least one of gray scale values or color values for each image element of image data included in the patient data, determining a plurality of similar patients from among a set of reference patients based on similarities between the target feature vector and corresponding feature vectors of reference patients among the set of reference patients, and determining the number of potential clinical outcomes based on clinical outcomes of the plurality of similar patients, calculate a respective probability for each corresponding potential clinical outcome among the number of potential clinical outcomes based on similarities between the target feature vector and corresponding feature vectors of the plurality of similar patients to obtain a plurality of probabilities, each respective probability being of the corresponding potential clinical outcome being indicated by the patient data, calculate an entropy reduction amount corresponding to each respective anamnestic question among the set of anamnestic questions, the entropy reduction amount corresponding to the respective anamnestic question being an amount by which an answer to the respective anamnestic question would reduce an entropy of a probability distribution, and the probability distribution including the plurality of probabilities, select a first anamnestic question corresponding to a highest entropy reduction amount from among the set of anamnestic questions, and the probability distribution including the plurality of probabilities, present the first anamnestic question to a user via the interface, receive a first answer to the first anamnestic question from the user via the interface, and adapt the plurality of probabilities based on the first answer.

* * * * *